United States Patent
Zagon et al.

(10) Patent No.: US 6,737,397 B1
(45) Date of Patent: May 18, 2004

(54) CONTROL OF CANCER GROWTH THROUGH THE INTERACTION OF [MET$^5$]-ENKEPHALIN AND THE ZETA RECEPTOR

(75) Inventors: Ian S. Zagon, Hummelstown, PA (US); Patricia J. McLaughlin, Harrisburg, PA (US); Jill P. Smith, Camp Hill, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/640,622

(22) Filed: Aug. 17, 2000

Related U.S. Application Data

(63) Continuation of application No. 08/827,841, filed on Mar. 27, 1997, now Pat. No. 6,136,780.
(60) Provisional application No. 60/015,193, filed on Mar. 29, 1996, and provisional application No. 60/025,922, filed on Sep. 11, 1996.

(51) Int. Cl.$^7$ ............................................. A61K 38/00
(52) U.S. Cl. ................... 514/2; 424/9.2; 424/185.1; 424/277.1; 530/302
(58) Field of Search ...................... 514/2; 530/302; 424/9.2, 185.1, 277.1

(56) References Cited

U.S. PATENT DOCUMENTS 5,562,654 A * 10/1996 Smith ...................... 604/892.1

OTHER PUBLICATIONS

Gura. Science, 1997, 278:1041–1042.*
Jain. Sci. Am., 1994, 271:58–65.*
Curti. Crit. Rev. in Oncology/Hematology, 1993, 14:29–39.*
Hartwell et al. Science, 1997, 278:1064–1068.*
Reilly, M. Clin. Pharmaco Kivet. 4:313–323, 1997.*
Zagon et al, Life Science, 43:1313–1318, 1988.*
Aylsworth et al. (1979) "Opiate Antagonists Can Inhibit Mammary Tumor Growth in Rats" *Proceedings of the Society for Experimental Biology and Medicine* 161:18–20.
Faith et al. (1988) "Inhibition of Pulmonary Metastases and Enhancement of Natural Killer Cell Activity by Methionine–Enkephalin" *Brain, Behavior and Immunity* 2:114–122.
Horn et al. (1989) "Lack of Effect of Opioid Antagonist, Naltrexone, on the *In Situ* Growth of C–1300, NIE–115 and NS206 Murine Neuroblastoma Tumor Cell Lines" *Life Sciences* 45:2539–2545.
Iishi et al. (1991) "Enhancement by Methionine Enkephalin of Colon Carcinogenesis Induced by Azoxymethane" *Cancer Research* 51:785–788.
Kikuchi et al. (1987) "Effects of Naloxone on Human Ovarian Cancer Cell Growth in Vitro and in Vivo" *Jpn. J. Cancer Res.* 78:519–525.

Kikuchi et al. (1989) "Inhibition of Human Ovarian Cancer Cell Proliferation in Vitro by Neuroendocrine Hormones" *Gynecologic Oncology* 32:60–64.
Koo et al. (1996) "Relative Efficacy of the Opioid Antagonist, Naltrexone, on the Initiation and Promotion Phases of Rat Mammary Carcinogenesis" *Anticancer Research* 16:1893–1898.
Lee et al. (1994) "Differential effects of Methionine Enkephalin on the Growth of Brain Tumor Cells" *Journal of Neuro–Oncology* 19:11–15.
Lewis et al. (1983) "Apparent Involvement of Opioid Peptides in Stress–Induced Enhancement of Tumor Growth" *Peptides* 4:635–638.
Lissoni et al. (1993) "Radioendocrine Therapy of Brain Tumors with the Long Acting Opioid Antagonist Naltrexone in Association with Radiotherapy" Ovid Citation 281 [http://ovid.hslc.org] abstract of *Tumori* 79(3):198–201.
Maneckjee et al. (1990) "Opioid and Nicotine Receptors Affect Growth Regulation of Human Lung Cancer Cell Lines" *Proc. Natl. Acad. Sci. USA* 87:3294–3298.
Mascarenhas et al. (1992) "Ihhibitory Effect of Tumor Growth by Methionine–enkephalin" (translated from Portuguese) Ovid Citation 83 [http://ovid.hslc.org] abstract of *Arquivos de Neuro–Psiguiatria* 50(1):84–90.
Murgo, A. (1985) "Inhibition of B16–BL6 Melanoma Growth in Mice by Methionine–Enkephalin" *JNCL* 75(2):341–344.
Murgo, A. (1986) "Effects of [Met]Enkephalin and Corticosterone on Thymus Weight and Tumor Growth" *Neuroendocrinol. Lett.* 8:79–85.
Murgo, A. (1989) "Modulation of Murine Melanoma Growth by Naloxone" *Cancer Letters* 44:137–142.
Scholar et al. (1987) "The Antimetastatic Activity of Enkephalin–Like Peptides" *Cancer Letters* 35:133–138.
Shavit et al. (1983) "Endogenous Opioids may Mediate the Effects of Stress on Tumor Growth and Immune Function" *Proc. West. Pharmacol. Soc.* 26:53–56.
Simon et al. (1984) "β–Endorphin Injected into the Nucleus of the Raphe Magnus Facilitates Metastatic Tumor Growth" *Brain Research Bulletin* 12:487–491.

(List continued on next page.)

*Primary Examiner*—Anthony C. Caputa
*Assistant Examiner*—Minh Tam Davis
(74) *Attorney, Agent, or Firm*—Scully, Scott, Murphy & Presser

(57) ABSTRACT

The present invention is related to the treatment and prevention of cancer including particularly gastrointestinal cancer. More specifically, the present invention describes the use of naltrexone, naloxone and the pentapeptide growth factor [Met$^5$]-enkephalin to inhibit and arrest the growth of cancer. Such efficiency has been discovered to be a consequence of the functional manipulation of the zeta (ζ) opioid receptor through endogenous [Met$^5$]-enkephalin. This receptor has been determined to be present in growing cancers such as pancreatic and colon cancer, for example.

5 Claims, 25 Drawing Sheets

OTHER PUBLICATIONS

Tejwani et al. (1989) "Naltrexone Inhibits Rat Mammary Tumorigenesis Induced by Stress and a Carcinogen" *Advances in the Bioscience* 75:615–618.

Zagon et al. (1989) "Characterization of Zeta (ζ): A New Opioid Receptor Involved in Growth" *Brain Research* 482:297–305.

Zagon et al. (1990) "Demonstration and Characterization of Zeta (ζ), a Growth–related Opioid Receptor, in a Neuroblastoma Cell Line" *Brain Research* 511:181–186.

Zagon et al. (1991) "Zeta (ζ), a Growth–related Opioid Receptor in Developing Rat Cerebellum: Identification and Characterization" *Brain Research* 551:28–35.

Zagon et al. (1993) "Production and Characterization of Polyclonal and Monoclonal Antibodies to the Zeta (ζ) Opioid Receptor" *Brain Research* 630:295–302.

Zagon et al. (1993) "Zeta (ζ), the Opioid Growth Factor Receptor: Identification and Characterization of Binding Subunits" *Brain Research* 605:50–56.

Behr et al., (1997), "Radioimmunotherapy of Solid Tumors: A Review 'Of Mice And Men'." *Hybridoma*, vol. 16 No. 1,pp. 101–107.

Bodey et al., (1996), "Human Cancer Detection And Immunotherapy With Conjugated And Non–Conjugated Monoclonal Antibodies." *Anticancer Research*, 16:661–674.

Clarke et al., (1996), "Human Breast Cancer Cell Line Xenografts As Models of Breast Cancer–The Immunobiologies of Recipient Mice And The Characteristics Of Several Tumorigenic Cell Lines." *Breast Cancer Research And Treatment*, 39:69–86.

Hytrek et al., (Oct. 1994), "Endogenous Opioid Systems And Human Colon Carcinomas Growth in Nude Mice." , *Lab Animal Sci.*, 33A–16.

Hytrek et al., (1995), Characterization of the Zeta (ζ) Opioid Receptor In Human Colon Cancer., *FASEB J.*, 9:A703.

Hytrek et al., (May 1995), "Opioid Growth Factor Modulates Tumorigenesis Of Human Colon Carcinomas Growth In Nude Mice." *Gastroenterology*, 108:A483.

Hytrek et al., (1996), "Identification And Characterization of ζ–Opioid Receptor In Human Colon Cancer." *Amer.J. Physiol.*, R115–R121.

Hytrek et al., (1996), "Inhibition Of Human Colon Cancer By Intermittent Opioid Receptor Blockade With Naltrexone." *Cancer Letters 101*, pp. 159–164.

Hytrek et al., (1996), "Inhibition of Human Clon Cancer By Naltrexone.", *Gastroenterology*, 110:A532.

Hytrek et al., "Presence of Opioid Growth Factor (OGF) And Zeta (ζ) Opioid Receptor, and the Autocrine Production of OGF, in human colon cancer cell in vitro." *FASEB J.*, 10:A181.

Royai et al., (Dec. 1996) "Preclinical Models Of Prostate Cancer." *Seminars in Oncology*, vol. 23, No. 6, Suppl. 14, pp. 35–40.

Wenisch, H.J.C., (1996), "Xenotransplantation of Human Thyroid Carcinomas In Anthymic Nude Mice." *Exp. Clin. Endocrinol Diabetes*, 104, Suppl. 3, pp.61–63.

Zagon et al., (Nov. 1987) "Opioid Receptors And Endogenous Opioids In Diverse Human And Animal Cancers.", *JNCI*, vol. 79, No. 5, pp. 1059–1065.

Zagon et al., (1995), "Opioid Growth Fsctor Modulates Corneal Epithelial Outgrowth In Tissue Culture." *Amer. Phys. Soc.*, pp. R942–R950.

Zagon et al., (1996), "Opioid Growth Factor ([Met5] Enkephalin) Prevents The Incidence And Retards The Growth Of Human Colon Cancer." *Amer. J. Physiol.*, pp. R780–R786.

Zagon et al., (1997), "Opioid Growth Factor (OGF) Inhibits Human Pancreatic Cancer Transplanted Into Nude Mice." *Cancer Letters* 112, pp. 167–175.

Zagon et al., (May 1995), "Pesence of OGF and Zeta (ζ) Opioid Receptor In HT–29 Human Colon Cancer." *Gastrienterology*, 108–A402.

Zagon et al., (1995), "OGF and the ζ Opionid Receptor Are Present And Function In Human And Mouse Epidermis.", *Mol.Biol.. Cell 6*, (Suppl.) 235a, Abstract No. 1362.

Zagon et al., (1996), "Opioid Growth Factor Inhibits The Growth of HT–29 Human Colon Cancer in Vitro." *FASEB J.*, 10:A181e.

Zagon et al., (1992), "Gastroenterology." 102:A299.

Zagon et al., (1993), "Brain Research." 630: 295–302.

* cited by examiner

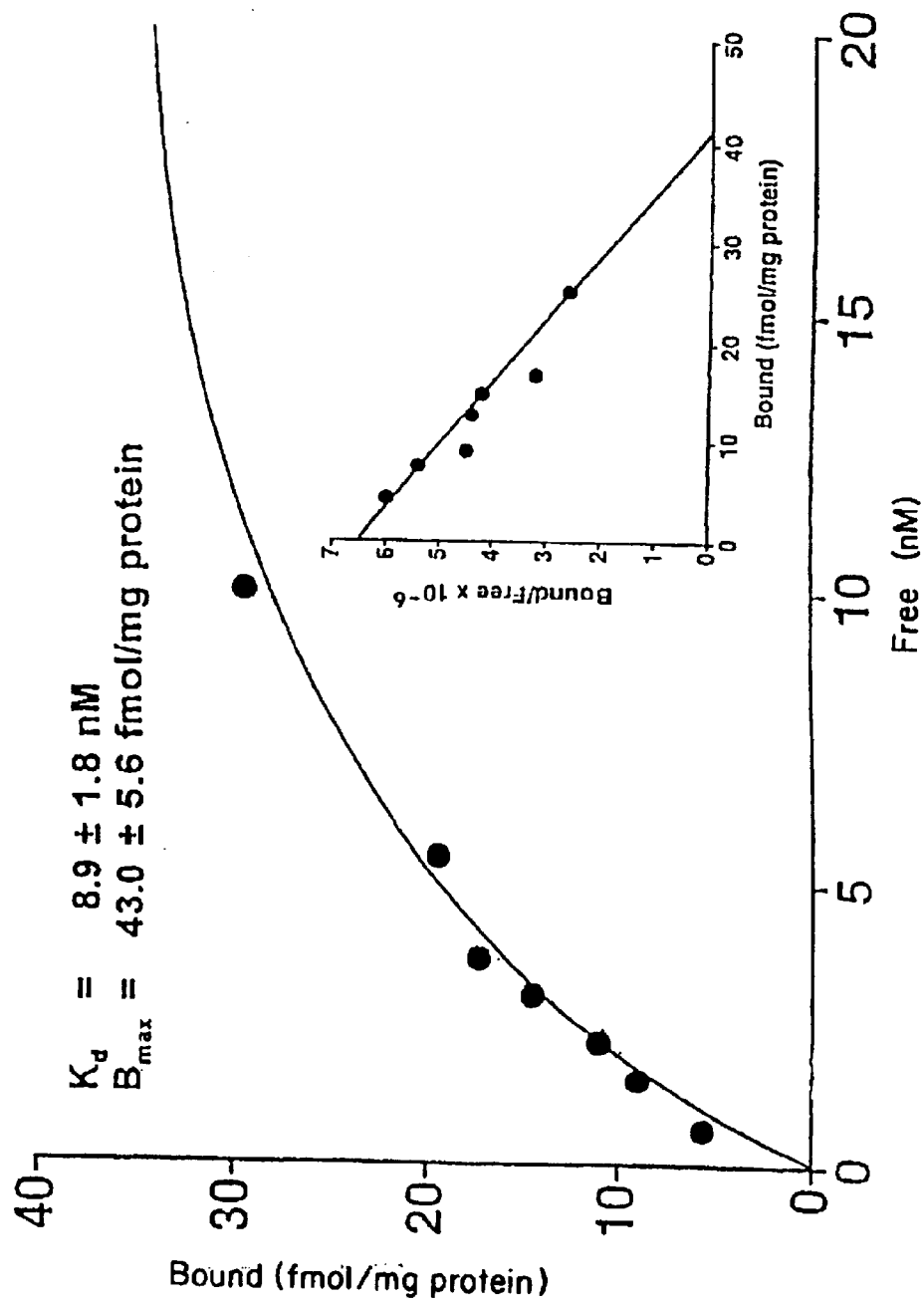

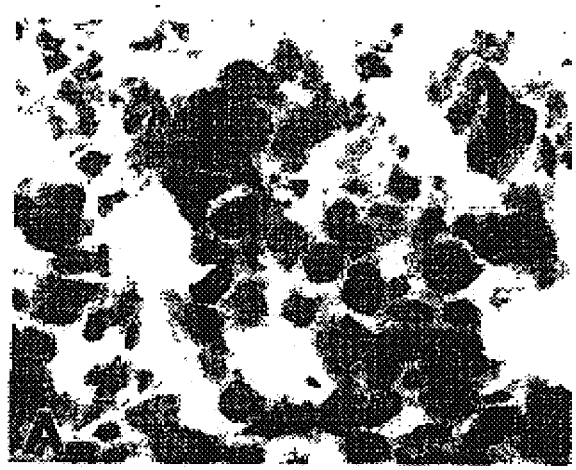
FIG.20A
 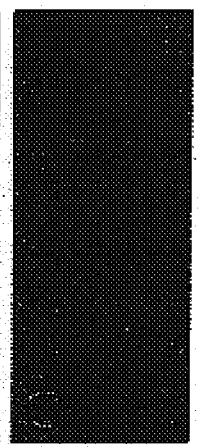
FIG.20B  FIG.20C
 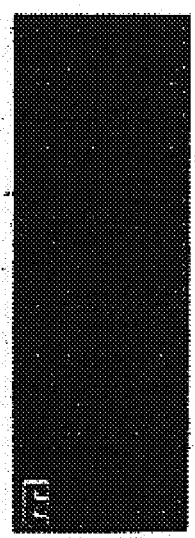
FIG.20D  FIG.20E

CONTROL OF CANCER GROWTH THROUGH THE INTERACTION OF [MET⁵]-ENKEPHALIN AND THE ZETA RECEPTOR

CROSS REFERENCE TO RELATED APPLICATIONS

This application is a continuation of application Ser. No. 08/827,841, filed on Mar. 27, 1997 now patented, U.S. Pat. No. 6,136,780, which claims the benefit of Provisional application Ser. Nos. 60/015,193, filed Mar. 29, 1996, and 60/025,922, filed Sep. 11, 1996.

BACKGROUND OF THE INVENTION

Cancer encompasses many disease states generally characterized by abnormally proliferating cells. Cancers are collectively the second leading cause of death in the United States today. While various conventional regimes to treat the myriad of cancers which affect the population including radiation, chemotherapy and surgery find limited success, no fundamental trait or characteristic has been associated with the wide array of cancers known today which has permitted an effective uniform and successful response to this disease state.

Gastrointestinal cancers, for example, represent a class of neoplasias affecting the population at rates which evidence little or no success by conventional treatment regimes. Some malignancies in this class have virtually little hope of successful treatment. Notably, for example, pancreatic cancer is a fatal malignancy occurring in over 28,000 Americans each year, and ranks as the fourth most common cause of cancer-related mortality in the United States. For reasons that are not entirely understood, the incidence of pancreatic cancer has tripled over the past four decades. The median of survival after diagnosis is 3–6 months, with a five-year survival rate of approximately 2%. In spite of treatment efforts including surgery, radiation and chemotherapy the survival rate has not changed significantly for decades.

Furthermore, approximately 160,000 new cases of colon and rectal cancer occur each year in the United States, and about 65,000 deaths are attributed annually to this disease. It is the second leading cause of cancer mortality in the United States. Despite its frequent occurrence and intense basic and clinical science research, the incidence and mortality rate of this disease have remained relatively stable over the past few decades.

Recently a number of growth factors have been identified to be associated with, and which may be important in, carcinogenesis, including neoplasias of the gastrointestinal tract. It has been shown, for example, that alteration-in these growth factors and/or their receptors could lead to disease states such as cancer, and thus may offer clues in the treatment of neoplasias. However, the data reflected in the literature extant evidences various circumstances which are entirely conflicting, evidencing both inhibition and acceleration of cell growth.

One group of peptides—the endogenous opioids—appears to be important in the growth of normal, neoplastic, renewing, and healing tissues, as well as in prokaryotes and other eukaryotic organisms. Most notably, the pentapeptide, [Met⁵]-enkephalin, has been identified as an endogenous opioid directly involved in growth processes, serving as a negative regulator in a wide variety of cells and tissues. Cell proliferation, as well as cell migration, differentiation, and survival, are influenced by this growth peptide. In view of a direct influence on the growth of neural and non-neural cells and tissues, and its non-modulatory action, [Met⁵]-enkephalin has been termed opioid growth factor (OGF). [Met⁵]-enkephalin interacts with δ and μ opioid receptors of neuronal cells when serving as a neurotransmitter.

In earlier work, the present inventors identified certain exogenous opioid antagonists including naloxone and naltrexone as effecting growth regulation in a wide array of cellular sources. For example, experiments utilizing a murine model of neuroblastoma and naltrexone, have shown that the effects of these antagonists depend on the duration of receptor blockade. Thus, in A/Jax mice inoculated with neuroblastoma, chronic receptor blockade using either a single drug concentration of 10 mg/kg per day or repeated injections of a low drug dosage of 0.1 mg/kg given 4 times daily accelerated the course of tumorigenesis and shortened survival. These data indicated that opioids are negative regulators of growth. A/Jax mice inoculated with neuroblastoma cells and receiving a single daily injection of 0.1 mg/kg naltrexone exhibited an antitumor effect (e.g. decreased tumor incidence). It is now understood that this drug dosage blocks the opioid receptors for 4–6 h/day, thereby producing a subsequent period of elevated enkephalin levels and/or receptor number and leading to a "supersensitivity" to endogenous enkephalins. Thus, there is a sufficient interval each day for the interaction of opioids and/or receptors to retard tumorigenic events by way of a supersensitive response.

While the prior art has reported various observations and interactions of endogenous opioids and certain exogenous opioid antagonists in the context of cell growth, prior investigations fail to evidence sufficient relationship between such opioids and/or antagonists to permit uniform and effective treatment of a wide array of cancers including particularly, for example, gastrointestinal cancers. Moreover, the inconsistencies which have been characteristic of the prior art have frustrated the determination of meaningful broad based regimes utilizing these growth factors and/or the interaction with their receptors.

It has presently been discovered that endogenous [Met⁵]-enkephalin interfaces with an opioid receptor (ζ) to modulate cellular growth and particularly the growth of cancerous tumors which surprisingly are uniformly characterized by the presence of such receptors. Furthermore, in accordance with the present invention, it has been demonstrated that tumor growth can be controlled, e.g. inhibited, by the manipulation of the interaction between the endogenous opioid, [Met⁵]-enkephalin and this newly discovered opioid receptor named the zeta (ζ) receptor. Identification of this receptor in growing cancer cells permits an understanding which, for the first time, facilitates meaningful broad based prevention, treatment and arrest of cancer.

SUMMARY OF THE INVENTION

It is an object of the present invention to provide methods for the prevention, treatment and arrest of cancers which are characterized by the presence of zeta receptors.

It is another object of the present invention to temporarily accelerate the growth of cancers which are characterized by the presence of a zeta receptor in order to treat such proliferating cells with chemotherapeutic agents which are efficacious against the cell proliferation of cancer.

These and other objects of the present invention are achieved by the administration of, or treatment with the opioid antagonist naloxone or naltrexone (or mixtures thereof) in an amount sufficient to effect the intermittent blockade of the zeta receptor present in the cancer cell (and surrounding tissue) thereby producing a subsequent period of elevated endogenous enkephalin levels or receptor numbers to inhibit, arrest and even prevent tumor growth. Alternatively, exogenous [Met$^5$]-enkephalin can be administered in amounts sufficient to occupy the zeta receptors of the tumor cell and thereby effect inhibition, arrest and even prevention of cancer cell growth.

Tumor cell proliferation, e.g. for targeting by chemotherapeutic agents such as cis-platin and adriamycin can be effected by either continuous blockade of the zeta receptor or other approaches which block endogenous [Met$^5$]-enkephalin interaction at the zeta receptor site.

BRIEF DESCRIPTION OF THE DRAWINGS

FIG. 9 graphically depicts representative saturation isotherm of specific binding of [$^3$H]-[Met$^5$]-enkephalin to HT-29 nuclear homogenates. Mean±SE binding affinity ($K_d$) and binding capacity ($B_{max}$) values from 8 experiments performed in duplicate are shown. Representative Scatchard plot (inset on right) of specific binding of radiolabeled [Met$^5$]-enkephalin to HT-29 homogenates revealed a one-site model of binding.

FIG. 20 are photomicrographs of sections from BxPC-3 human pancreatic tumors transplanted into nude mice using brightfield (A) or indirect immunofluorescent (B-E) optics. (A) Section stained with hematoxylin and eosin showing a well-differentiated adenocarcinoma with gland-forming areas composed of columnar epithelial cells without keratinization; note band of fibrous connective tissue separating nests of tumor cells. (B,D) Specimens stained with antibodies to the OGF. [Met$^5$]-enkephalin (B) or ζ-opioid receptor (D) cells, and showing the immunoreactivity associated with the cytoplasm of the tumor cells and lack of staining of the nucleus. (C,E) Control sections stained with antibodies to [Met$^5$]-enkephalin (C) or ζ-opioid receptor (E) preabsorbed with pure antigens ([Met$^5$]-enkephalin (C) or the 17-kDa subunit of the ζ receptor (E)). Bar=38 µm.

DETAILED DESCRIPTION OF THE INVENTION

Figure 1:
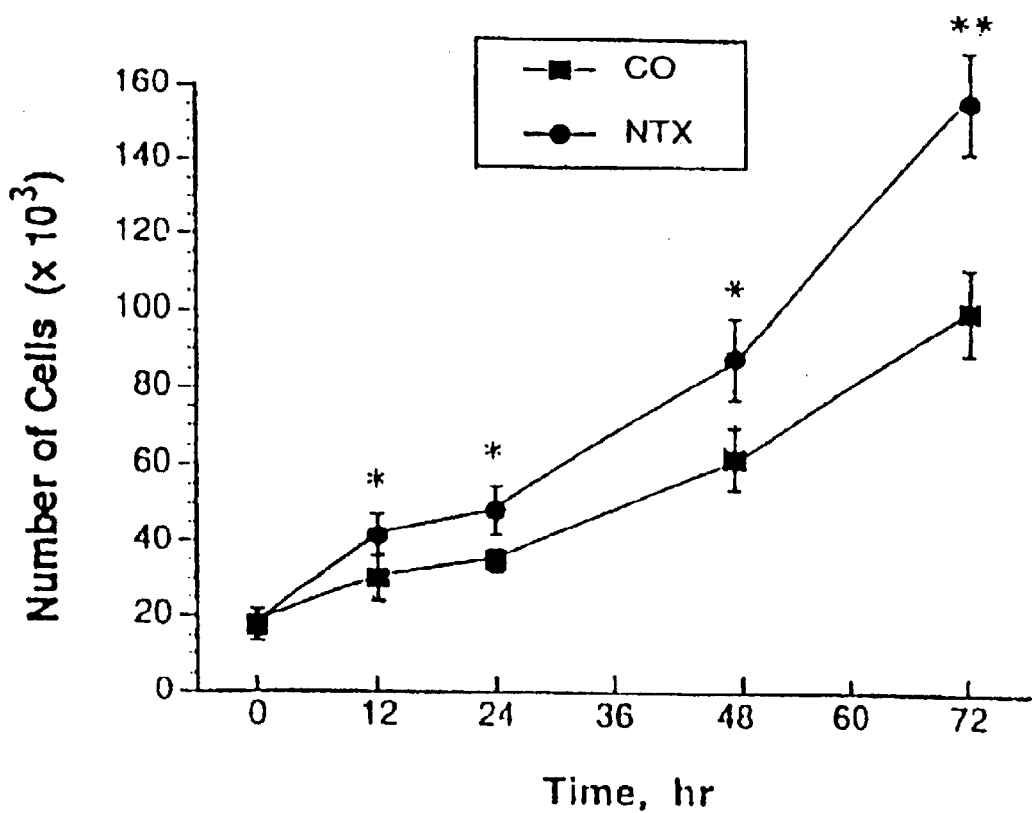
FIG. 1 graphically depicts the growth of HT-29 cells subjected to 10$^{-6}$ M NTX. Twenty-four hours after seeding (=0 hr), NTX or an equivalent volume of sterile water (CO) were added; media and NTX were changed daily. Data represent means±SE for at least 2 aliquots/well from 2 wells/group/time point. Significantly different from controls at $p<0.05(*)$ and $p<0.01(**)$.

In accordance with the present invention, it has been demonstrated that endogenous [Met$^5$]-enkephalin interfaces with a recently identified opioid receptor called the zeta (ζ) receptor to modulate cellular growth of cancerous tumors. Surprisingly, this zeta (ζ) receptor has been determined to be both present and functional in growing cancer cells. Unlike other opioid receptors such as µ, δ and κ which are membrane associated, the zeta receptor has been identified in the nuclear compartment of tumor cells. In normal tissue the zeta receptor is an approximately 220 kD protein comprised of at least 4 subunits of 32, 30, 17 and 16 kD which are known to bind [Met$^5$]-enkephalin.

As a consequence of this discovery, the present inventors have provided a broad based, yet fundamental, regime to treat the occurrence of growing cancers wherein the single qualification for such treatment is that the cancer is characterized by the presence of the zeta receptor. For example, one skilled in the art can readily determine the presence of such zeta receptors by conventional techniques such as receptor binding assays using radiolabeled [Met$^5$]-enkephalin or by using labeled antibodies to the zeta-receptor which are available to the skilled artisan.

For the purposes of this application, the term "treatment" of cancer means the prevention of the onset of cancer; the inhibition of the growth of existing cancer; the prevention of the reoccurrence of cancer; and the total arrest of cancer. The prevention of the reoccurrence of cancer contemplates cancer sites and surrounding tissue which have previously been treated by radiation, chemotherapy, surgery or other techniques. Prevention also includes circumstances of prophylaxes where the onset of oncogenesis or tumorigenesis is not evidenced in the patient such as circumstances where a predisposition for cancer is identified whether determined by genetic screening, for example, or otherwise.

For the purposes of this application, cancer means any cancer which is characterized by the presence of at least one zeta receptor whether manifest in an adult, pediatric or fetal patient.

The methods of the present invention are thus applicable to a wide array of cancers and particularly gastrointestinal cancers. Gastrointestinal cancers include pharyngeal, esophageal, stomach, small and large intestine, liver, rectal, colon, pancreatic (particularly ductal tumors), biliary tract cancers including gall bladder and bile duct cancers. These cancers may be squamous or adenocarcinoma and particularly include solid tumors. Other cancers which can be treated in accordance with the present invention include, for example, head and neck cancers and breast cancer.

The regimes offered by the present invention do not dissipate or reduce a tumor mass or other metastasized growth once established and thus are likely to be used in those circumstances with other therapies such as surgery, e.g. tumor excision, chemotherapy and radiation. The compounds and implemented methods of treatment of the present invention can arrest tumor growth and inhibit continued growth of the abnormal cells thus reducing tumor burden. In other circumstances such as treatment prior to tumorigenesis or after tumor excision, for example, the methods of the present invention can prevent oncogenesis or tumor regrowth, respectively.

The treatment and methods of the present invention are effected through the controlled manipulation of endogenous levels of [Met$^5$]-enkephalin. [Met$^5$]-enkephalin has been identified as endogenous negative growth regulator, often called opioid growth factor (OGF) due to its non-neurotransmitting function and distribution in other than neurotransmitter cells.

OGF serves as a modulating agent in cell proliferation as well as cell migration, differentiation and survival. In accordance with the present invention, it has been determined that OGF interacts with the newly identified zeta receptor, an opioid receptor, which is nuclear associated. Moreover, the zeta receptor has been determined by the present invention to be characteristic of growing cancer cells. Accordingly, it has been demonstrated (see Examples) that OGF is a regulator of cancer growth and formation, serving to continually repress the biological events associated with oncogenesis. Tumor incidence and growth therefore are a function of the interface (effecting interaction or binding) between OGF and the zeta receptor.

Specifically, when this-interaction is blocked or disabled, e.g. by insufficient production of endogenous [Met$^5$]-enkephalin (OGF) or as a consequence of defective receptors, neoplasias and cancerous cell proliferation can be commenced and/or stimulated. The addition of exogenous [Met5]-enkephalin (OGF) or the stimulation of a heightened production of endogenous OGF negatively regulates the growth of cancer directly by occupying available receptor sites and/or by initiating the growth and availability of additional zeta receptor sites.

Accordingly, cancers characterized by the presence of at least one functional zeta receptor, including particularly gastrointestinal cancers and especially colorectal cancers and pancreatic cancer can be treated by the exogenous administration of [Met$^5$]-enkephalin (OGF) Regimes in cumulative amounts ranging from about 0.1 to about 10 mg of exogenous OGF per day for a human patient is effective. (These amounts have been observed to be about 1000 fold more than normal plasma levels.) Such regimes provide sufficient amounts of OGF to occupy the zeta receptors and effectively arrest the continued growth of the cancerous growth.

Manipulation of the zeta receptor in a manner affecting the endogenous production of OGF and the interface between OGF and the zeta receptor can also effect treatment of growing cancers in accordance with the present invention. Specifically, the opioid antagonists naloxone (NAL) and naltrexone (NTX) can be used to blockade the zeta receptor in a manner producing elevated levels of endogenous [Met$^5$]-enkephalin. More specifically, it has been determined in accordance with the present invention that intermittent or temporary blockade of the zeta receptor (stereospecifically) with naloxone or naltrexone induces elevated levels of endogenous [Met$^5$]-enkephalin and/or elevated numbers of zeta receptors. Thus, cancer growth can be inhibited and arrested by the interaction of induced increased levels of the endogenous product and receptor. It is also observed that such manipulation not only produces heightened levels of OGF and zeta receptors but also increases the cells "sensitivity" or "susceptibility" to the molecule as part of the efficacy.

Regimes ranging in cumulative amounts from about 0.1 to about 10 mg per day of naltrexone or naloxone for a human patient can effect successful inhibition and arrest in the treatment of growing cancer.

The compounds of the present invention can be administered intravenously, orally or parenterally. Time-release administration of naloxone, naltrexone or OGF in many circumstances is advantageous and can be administered using a time-release patch, microcapsules, spherical bead implants, suspensions, osmotic pumps and other conventional means, for example. In some circumstances direct application of OGF to a tumor site is preferred.

In another embodiment of the present invention, growing cancer which is characterized by the presence of zeta receptors can be treated by blocking or interrupting the interaction of endogenous [Met$^5$]-enkephalin with the zeta receptor. In the first instance, this technique elicits cell proliferation of the identified cancer. Subsequently, however, the patient is administered an anti-cancer drug, such as, for example, cis-platin, which is efficacious against cell proliferation. Such inducement of cell proliferation prior to treatment with an anti-cancer drug which "acts" upon the proliferating cells provides improved results since the cancer cells are brought to a critical and uniform level prior to administration of the anti-cancer drug thus permitting the anti-cancer drug to be more effective.

Interruption or blockade of the interaction between endogenous [Met$^5$]-enkephalin and the zeta receptor can be effected by the administration of naloxone or naltrexone in amounts which sufficiently blockade the zeta receptor from interaction with endogenous OGF. Subsequently, the patient is administered an anti-cancer drug such as cis-platin, which is efficacious against proliferating cells.

In this method, naloxone or naltrexone are administered in cumulative amounts of at least about 20 mg to about 600 mg or more per day to effect continuous blockade of the involved zeta receptors. Regimes of about 20 to about 150 mg per day are preferred to cause proliferation of the cancer cells such that the proliferating cells can be subsequently treated with an anti-cancer drug. Treatment with the selected anti-cancer drug can be simultaneous with, or subsequent to, administration of the opioid antagonist, although some delay is preferred.

Interruption of the interface between endogenous [Met$^5$]-enkephalin and the zeta receptor of the involved cancerous tissue can also be altered or disrupted by disrupting the translation or transcription of either the zeta receptor or the endogenous OGF. Such technique inhibits the production and thus availability of the related molecules. Transcription and translation of the OGF or the, zeta receptor can be interrupted by manipulations known to those skilled in the art such as anti-sense technology, for example. Anti-enkephalinases can be administered in order to maintain the desired levels of OGF (post-translationally). Moreover, antibodies to the zeta-receptor or [Met$^5$]-enkephalin are available and can be provided to the cancerous site thus blocking the interaction between the OGF and its receptor.

For a better understanding of the present invention together with other and further objects, reference is made to the following descriptions and examples.

EXAMPLE 1

[Met$^5$]-Enkephalin Inhibits Colon Cancer 1-1. Cells, Cell Culture, and Drugs

HT-29, WiDr, and COLO 205 cell lines were obtained from the American Type Culture Collection (Rockville, Md.). HT-29 cells were grown in McCoy's 5A media (modified), WiDr cells in Minimum Essential Media, and COLO 205 cells in RPMI 1640 media; all media contained 10% fetal calf serum, 2 mM ζ-glutamine, 1.2% sodium bicarbonate and antibiotics (11 Units/ml penicillin, 10 $\mu$g/ml streptomycin, 10 $\mu$g/ml neomycin) in a humidified atmosphere of 7% $CO_2$/93% air at 37° C. In some examples, cultures of HT-29 cells were maintained in McCoy's 5A media without fetal calf serum.

[$^3$H]-[Met$^5$]-enkephalin was obtained from DuPont-New England Nuclear (Boston, Mass.). [Met$^5$,Arg$^6$,Gly$^7$,Leu$^8$]-enkephalin (octapeptide, proenkephalin), naltrexone hydrochloride, phenylmethylsulfonyl-fluoride (PMSF), somatostatin, Sigma Chemical (St. Louis, Mo.); morphine sulfate, Mallinkrodt (St. Louis, Mo.); cholecystokinin-8 (CCK-8), dynorphin A 1–8, gastrin, thiorphan, U69,593, Peninsula Laboratories (Belmont, Calif.); (−)-naloxone hydrochloride, (+)-naloxone hydrochloride, SKF-10,047, National Institute on Drug Abuse (Rockville, Md.); β-endorphin, Bachem (Torrence, Calif.); guanylyl-imidodiphosphate (GppNHp) tetralithium salt, Boehringer Mannheim (Indianapolis, Ind.).

1-2. Growth Assays

Cells were seeded at equivalent amounts into 75 cm$^2$ flasks or into 9.6 cm$^2$ wells (6-well plates, Falcon) and were counted 24 hr later to determine plating efficiency. Drugs or sterile water were added beginning 24 hr after seeding (=0 hours) and both media and drugs were changed daily. All drugs were prepared in sterile water and dilutions represent final concentrations of the compounds. At appropriate times, cells were harvested with 0.05% trypsin/0.53 mM EDTA, centrifuged, and counted with a hemacytometer at 200×. Cell viability was determined by trypan blue staining. At least 2 aliquots/flask or well were counted and 2 flasks or wells/time point/treatment group were sampled.

To examine the presence of the [Met$^5$]-enkephalin, and the ζ-opioid receptor, log phase HT-29 cells were examined 72 hr after seeding. Cells were fixed and permeabilized in 95% ethanol and acetone at −20° C., rinsed in Sorenson's phosphate buffer (SPB), and blocked with SPB and 3% normal goat serum and 0.1% Triton X-100 at room temperature for 15 minutes. Ammonium sulfate purified anti-[Met$^5$]-enkephalin IgG or anti-ζ-receptor IgG were diluted (1:100) in SPB with 1% normal goat serum in 0.1% Triton X-100. Details about the production and characteristics of the polyclonal antibodies to [Met$^5$]-enkephalin (CO-172) and ζ-receptor (AO-440) have been reported elsewhere (e.g., Zagon, I. S., Y. Wu and P. J. McLaughlin, *Am.J. Physiol.* 267:R645–R652 (1994); Zagon, I. S. and P. J. McLaughlin, *Brain Res.* 630:295–302 (1993).

1-3. Receptor Binding Assays

Log phase cells were incubated in 0.05% trypsin for at least 30 min with gentle agitation at 37° C. in order to reduce clumping of cells and facilitate isolation of cell nuclei. Preparations were homogenized (Polytron, setting 6, 2×10 sec) in a 1:20 (wt/vol) solution (=Tris/all) of cold 50 mM Tris HCl buffer with 0.1 mg/ml bacitracin, 1 $\mu$g/ml leupeptin, 60 nM thiorphan, 1 mM EGTA, and 0.6 mg/l PMSF, pH 7.4, at 4° C. The homogenates were layered over a 1.4 M sucrose cushion and centrifuged (2,200×g) for 20 min; this step was carried out twice to obtain a nuclear pellet (P1). Protein homogenates of P1 were diluted with Tris/all and incubated at room temperature (22° C.) for 20 min to remove endogenous opioid peptides. Aliquots of protein in 0.95 ml Tris/all were incubated with agitation for 90 min at 22° C. with 50 $\mu$l of [$^3$H]-[Met$^5$]-enkephalin.

Saturation assays were conducted using a variety of concentrations of ligand usually ranging from 0.1 to 15 nM. The final volume of the incubation mixture was 1 ml. The incubation was terminated by rapid filtration through Whatman GF-B filters under vacuum pressure with a Brandel Cell Harvester. Filters were rinsed three times with 5 ml volumes of ice-cold 50 mM Tris buffer, dried at 60° C. for 1 hour, and counted in a 2:1 solution of Aquasol-toluene by liquid scintillation spectrometry (Beckman LS-2800). Non-specific binding was determined in the presence of 100 nM of [Met$^5$]-enkephalin. Duplicate tubes of homogenates were assayed for each-concentration utilized. Protein concentrations were determined by the BioRad method with gamma globulin as a standard.

Protein homogenates were diluted with Tris/all to the appropriate protein concentration and incubated at room temperature (22° C.) for 20 minutes to remove endogenous opioid peptides. Aliquots of protein in 0.95 ml Tris/all were incubated with agitation for 150 minutes at 22° C. with 50 $\mu$l of [$^3$H]-[Met$^5$]-enkephalin. Saturation assays were conducted using a variety of concentrations of ligand usually ranging from 0.1 to 15 nM. The final volume of the incubation mixture was 1 ml. The incubation was terminated by rapid filtration through Whatman GF-B filters under vacuum pressure with a Brandel Cell Harvester. Filters were rinsed three times with 5 ml volumes of ice-cold 50 mM Tris buffer, dried at 60° C. for 1 hour, and counted in a 2:1 solution of Aquasol-toluene by liquid scintillation spectrometry (Beckman LS-2800). Non-specific binding was determined in the presence of 100 nM of [Met$^5$]-enkephalin. Duplicate tubes of homogenates were assayed for each concentration utilized. Protein concentrations were determined by the BioRad method with gamma globulin as a standard. To assess the presence and characteristics of $\mu$, δ and κ opioid receptors, were utilized. For these assays, non-specific binding was determined in the presence of 100 nM of DAMGO, DPDPE, or U69,593.

To determine the levels of the [Met$^5$]-enkephalin, [Met$^5$]-enkephalin, in the cells and media, log phase cultures of HT-29 cells were harvested and [Met$^5$]-enkephalin was extracted with cold 0.2 N HCl. Fresh media, and media from cultures incubated with cells for 4 hr, also were assayed. All assays for [Met$^5$]-enkephalin were performed with a radioimmunoassay kit from INCstar (Stillwater, Minn.). Specificity of the assay was 100% activity for [Met$^5$]-enkephalin and a cross-reactivity of 2.8% with [Leu$^5$]-enkephalin, 0.1% with α-endorphin (β-lipotropin), and less than 0.002% with β-endorphin, α-neo-endorphin, substance P, and porcine dynorphin. Each sample was evaluated in triplicate and two independent assays were performed.

1-4. Chemicals

The following compounds were obtained from the indicated sources: [Met$^5$]-enkephalin, [Leu$^5$]-enkephalin, [Des-Met$^5$]-enkephalin, [D-Pen$^{2,5}$]-enkephalin (DPDPE), BAM12P, [D-Ala$^2$,MePhe$^4$,Glyol$^5$]-enkephalin (DAMGO), β-endorphin, Sigma (St. Louis, Mo.); morphine sulfate, naltrexone, naloxone, (+)-SKF-10,047 (SKF-10,047), National Institute on Drug Abuse (Rockville, Md.); U50, 488, Upjohn Diagnostics (Kalamazoo, Mich.); dynorphin A1–13, peptide F, Peninsula (Belmont, Calif.); ICI 174,864 (Cambridge Research Biochemicals (Valley Stream, N.Y.); ethylketocyclazocine (EKC), Sterling-Winthrop (Rensslaer, N.Y.).

1-5. Animals and Tumors

HT-29 human colon cancer cells were grown in McCoy's 5A media (modified) containing 10% fetal calf serum, L-glutamine (2 mM), penicillin (10 units/ml), and streptomycin (100 μg/ml) in an atmosphere of 7% $CO_2$ at 37° C. Cell viability was determined by the trypan blue exclusion test. Five to six-week-old male athymic nude mice were injected subcutaneously over the right shoulder with 1×10$^6$ log phase HT-29 cells in a 0.5 ml volume of media. Fifty days after tumor cell inoculation, the mice were euthanized with $CO_2$ and tumor tissue was excised; skin, hair, and necrotic portions of the neoplasia were removed and the tissue was immediately frozen in liquid nitrogen. The tumors were stored at −70° C. until binding studies were conducted. All binding assays were performed within 3 months of tissue collection.

Human colon tumor tissue obtained from surgical resection also was utilized in this study. Research protocols were approved by the Clinical Investigation Committee of The Milton S. Hershey Medical Center of The Pennsylvania State University. The tumor tissue was stored at −70° C. for no more than 7 days before binding assays were performed. The histology of adenocarcinomas was confirmed by examination of hematoxylin and eosin stained sections. Preparations of protein fractions. Tumor tissue was weighted and homogenized (Polytron, setting 6, 2×10 sec) in a 1:20 (wt/vol) solution of cold 50 mM Tris-HCl buffer with 0.1 mg/ml bacitracin, 1 μg/ml leupeptin, 6 nM thiorphan, 1 mM EGTA, and 0.6 mg/l PMSF, pH 7.4 at 4° C.; this buffer will be termed Tris/all. The homogenates were filtered with sterile cheesecloth and centrifuged (39,000×g) for 20 minutes. The pellets were rehomogenized in 0.32 M sucrose, layered over a 1.4 M sucrose cushion, and centrifuged (2,200×g) for 20 minutes; this step was carried out twice to obtain a nuclear pellet (P1). For subcellular fractionation studies, the supernatant of P1 was centrifuged (39,000×g) for 20 minutes to obtain a plasma membrane pellet (P2). Following that spin, the supernatant was centrifuged overnight (100,000×g) resulting in a microsomal pellet (P3) and soluble supernatant (S3). All fractions were inspected for purity by phase microscopy.

1-6. Data Analysis

Cell numbers and radioimmunoassay data were analyzed using analysis of variance (one- and two-factor analysis where appropriate) with subsequent comparisons made with Newman-Keuls tests. Receptor binding data were analyzed with the Lundon I (Saturation Isotherm Binding Analysis) computer program (Lundon Software, Cleveland, Ohio). This analysis utilizes non-linear least-squares regression. Binding isotherms and Scatchard plots were computed directly by this program. Competition data were, analyzed by the Lundon II competition data-analysis program, and the inhibition constant ($K_i$) was calculated from the half-maximal displacement ($IC_{50}$) values using the method of Cheng and Prusoff.

EXAMPLE A

Opioid Anagonists and HT-29 Growth

Experiments were performed to ascertain whether opioids govern the growth of human colon cancer cells. Using a paradigm of blocking opioid-receptor interaction with a long-acting opioid antagonist, addition of 10$^{-6}$ M naltrexone (NTX) to HT-29 cultures resulted in an increase in cell number as compared to control levels (FIG. 1). Within 12 hr there were 38% more cells in cultures receiving NTX than in control cultures. At 24, 48, and 72 hr after daily addition of NTX and fresh media, the HT-29 cells exhibited increases in number ranging from 38% to 55% of control values.

EXAMPLE B

Determination of the Opioid Peptide(s) Related to Colon Cancer Cell Growth

To determine which opioid peptide(s) is(are) related to decreasing cell number, cultures of HT-29 cells were treated with 10$^{-6}$ M concentrations of a variety of opioid compounds (synthetic and natural) for 48 hr; dosages and times were based on previous studies (Zagon, I. S., and P. J. McLaughlin, and P. J. McLaughlin, The Role of Endogenous Opioids and Opioid Receptors in Human and Animal Cancers, In: Stress and Immunity, edited by N. P. Plotnikoff, A. J. Murgo, R. E. Faith, and J. Wybran. Caldwell, N.J.:CRC Press, 1991, p. 343–356.). The effects of various opioids on the number of HT-29 cells are presented in Table 1.

TABLE 1

| Opioid compounds having no effect on the number of HT-29 human colon cancer cells in culture |
|---|
| Opioid Compound |
| μ-Receptor |
| DAMGO |
| Morphine |
| δ-Receptor |
| DPDPE |
| ICI-174,864 |
| κ-Receptor |
| Dynorphin A(1–3) |
| U-50,488 |
| EKC |
| ε-Receptor |
| β-Endorphin |
| σ-Receptor |
| SKF-10,047 |
| Others |
| BAM12P |

TABLE 1-continued

Opioid compounds having no effect on the
number of HT-29 human colon cancer cells in culture Opioid Compound

[Des.-Met$^5$]enkephalin-
[Leu$^5$]enkephalin

All compounds were tested at a concentration of 10$^{-6}$M and cells were counted at 48 and 72 h after drug exposure in log phase cultures; drug and media were replaced daily. When possible; the compounds have been arranged with regard to receptor selectivity, but this does not indicate exclusivity. DAMGO, [D-Ala$^2$,N-Me-Phe$^4$,Gly$^5$ollenkephalin; DPDPE, [D-Pen$^{2-5}$]enkephalin; EKC, ethyl-ketocyclazocine.

Only the [Met$^5$]-enkephalin influenced growth and a statistically significant (p<0.01) decrease of 35% in cell number from control values of 5.6±0.2 million cells was noted. As mentioned earlier, this peptide has been previously termed the opioid growth factor ([Met$^5$]-enkephalin) to designate its function as growth factor in neural, non-neural, normal, and tumorigenic tissues and cells (Zagon, I. S., and P. J. McLaughlin, *Brain Res.* 542:318–323, 1991, Zagon, I. S., and P. J. McLaughlin, The Role of Endogenous Opioids and Opioid Receptors in Human and Animal Cancers, In: Stress and Immunity, edited by N. P. Plotnikoff, A. J. Murgo, R. E. Faith, and J. Wybran. Caldwell, NJ:CRC Press, 1991, p. 343–356, Bartolome, J. V., M. B. Bartolome, B. A. Lorber, S. J. Dileo, and S. M. Schanberg, Effects of Central Administration of Beta-Endorphin on Brain and Liver DNA—Synthesis in Preweaning Rats, *Neuroscience* 40:289–294, 1991; such terminology was employed in the present report.

EXAMPLE C
Evaluation of [Met$^5$]-Enkephalin and the Growth of HT-29 Cells

Figure 2:
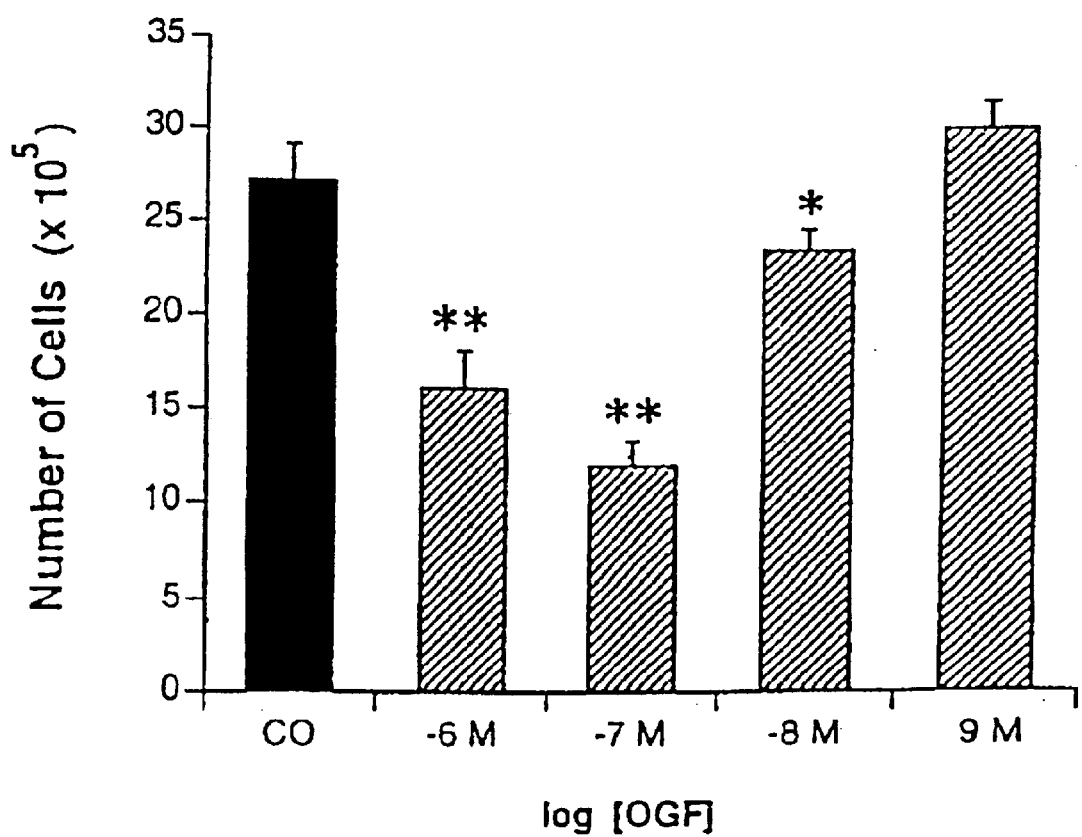
FIG. 2 graphically depicts the growth of HT-29 cells subjected to various concentrations of [Met$^5$]-enkephalin for 48 hr. [Met$^5$]-enkephalin or an equivalent volume of sterile water (CO) were added 24 hr after seeding, and media and [Met$^5$]-enkephalin were changed daily. Data represents means±SE for at least 2 aliquots/well from 4 wells/group. Significantly different from controls at $p<0.05(*)$ and $p<0.01(**)$.

To further define the extent of [Met$^5$]-enkephalin action in HT-29 human colon cancer cell growth, the effect of a variety of dosages of [Met$^5$]-enkephalin on the growth of log phase cells was monitored 48 hr after initiation of drug exposure (FIG. 2). Concentrations of 10$^{-6}$ M and 10$^{-7}$ M [Met$^5$]-enkephalin reduced the number of colon cancer cells by 41% and 56%, respectively, with a subnormal number of cells also detected for cultures exposed to 10$^{-6}$ M [Met$^5$]-enkephalin (a 14% reduction from control levels). HT-29 cell cultures treated with 10$^{-9}$ M [Met$^5$]-enkephalin were comparable to controls in cell number.

Figure 3:
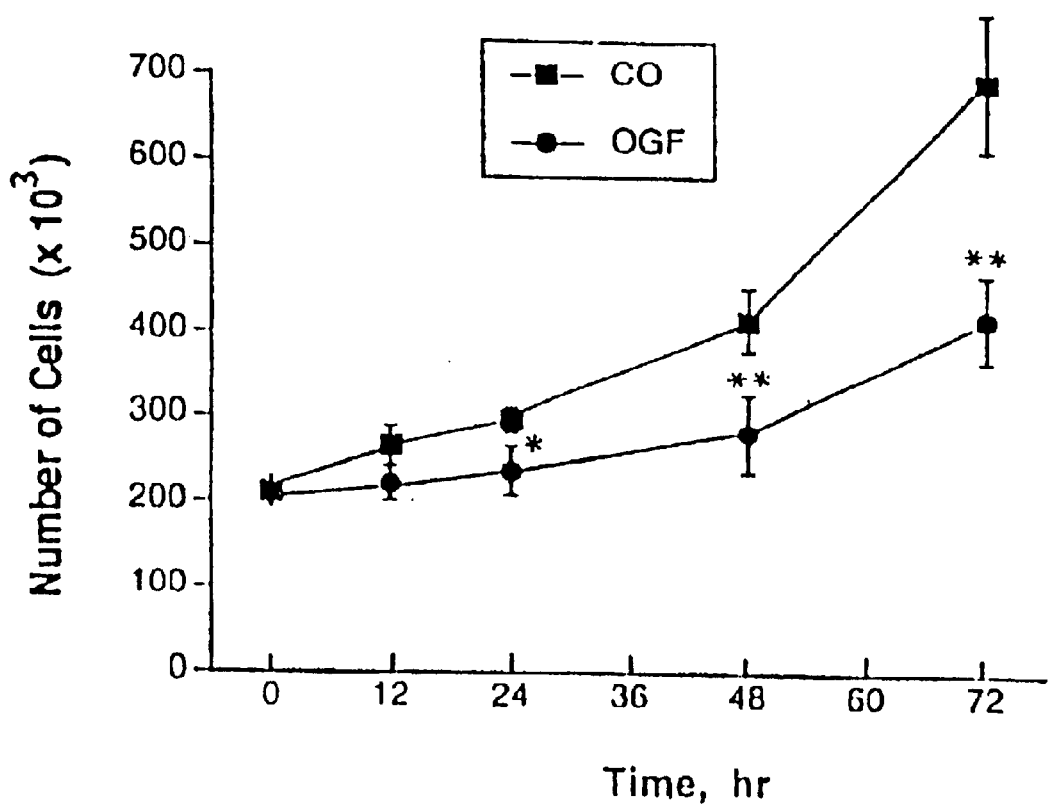
FIG. 3 graphically depicts the growth of HT-29 cells subjected to 10$^{-6}$ M [Met$^5$]-enkephalin over a 72-hour period of time. [Met$^5$]-enkephalin or an equivalent volume of sterile water (CO) were added 24 hr after seeding (=0 hr); media and [Met$^5$]-enkephalin were changed daily. Data represents means±SE for at least 2 aliquots/well from 2 wells/group/time point. Significantly different from controls at $p<0.05(*)$ and $p<0.01(**)$.

To examine the magnitude and duration of the inhibitory effects of [Met$^5$]-enkephalin on colon cell growth, log phase cells were exposed to 10$^{-6}$M [Met$^5$]-enkephalin for 72 hr (drug and media were replaced daily); these data are presented in FIG. 3. Within 12 hr of drug exposure cell number are decreased 17% from control levels, and marked reduction of 29%, 32%, and 41% were noted at 24, 48, and 72 hr, respectively.

Figure 4:
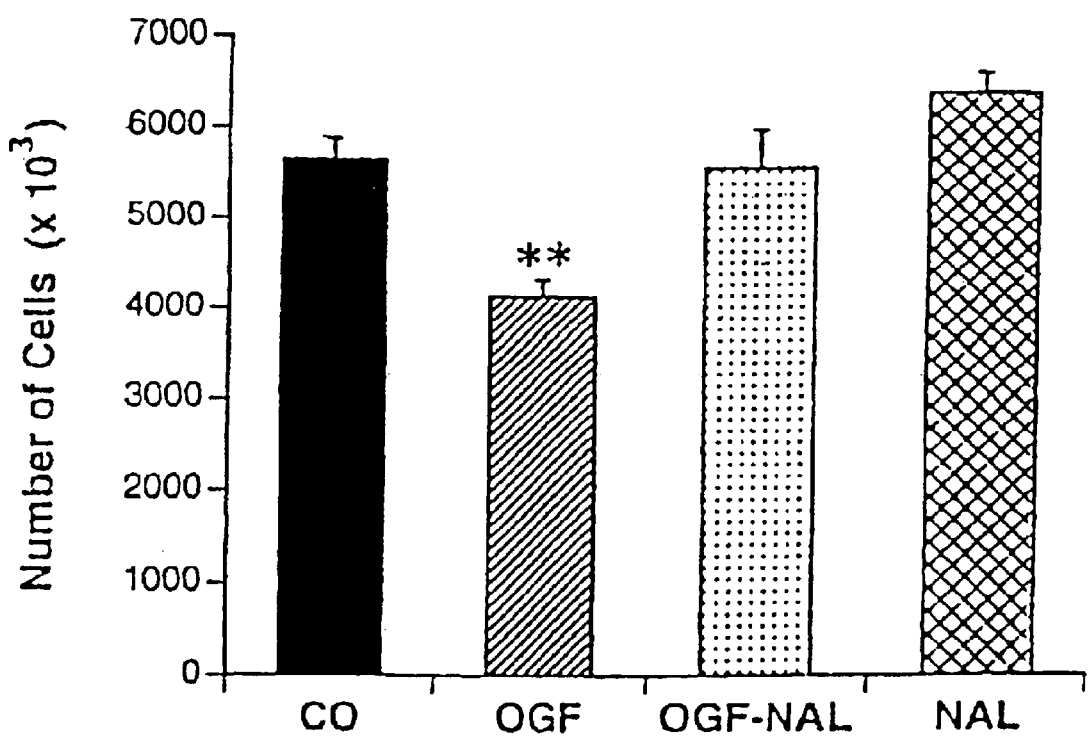
FIG. 4 graphically depicts the number of cells in HT-29 cultures 48 hr after being subjected to 10$^{-6}$ M concentrations of [Met$^5$]-enkephalin, [Met$^5$]-enkephalin and the opioid antagonist naloxone (NAL), or only NAL; an equivalent volume of sterile water was added to the control cultures (CO). Drugs were added 24 hr following seeding and both media and drugs were changed every 24 hr. Data represent means±SE for at least 2 aliquots/well from 2 wells/group/time point. Significantly different at $p<0.01(**)$.

To examine whether the inhibitory effect of [Met$^5$]-enkephalin on cell number in HT-29 human colon cancer cells was mediated by an opioid receptor, cultures were treated with both [Met$^5$]-enkephalin (10$^{-6}$ M) and the short-acting opioid receptor antagonist, naloxone (10$^{-6}$ M) (FIG. 4). Other cultures received only naloxone (10$^{-6}$ M), only [Met$^5$]-enkephalin (10$^{-6}$ M), or sterile water; 48 hr later cell number was assessed. [Met$^5$]-enkephalin inhibited cell number by 21%, and concomitant administration of [Met$^5$]-enkephalin and the antagonist blocked the inhibitory effects of [Met$^5$]-enkephalin. Naloxone alone, at the dosage utilized, had no effect on cell growth.

EXAMPLE D
Reversal of [Met$^5$]-Enkephalin Inhibition

Figure 5:
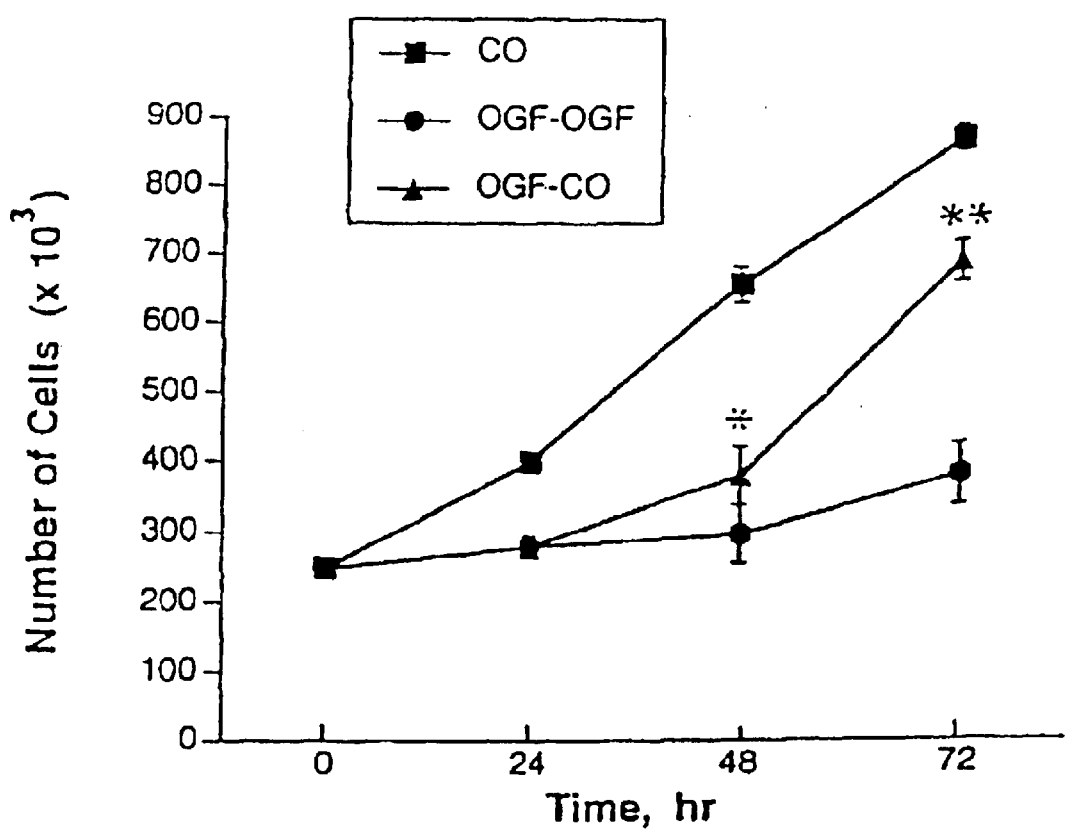
FIG. 5 graphically depicts the reversibility of [Met$^5$]-enkephalin-induced growth inhibition in HT-29 colon cancer cells. Cells were seeded and, 24 hr later (=0 hr), [Met$^5$]-enkephalin (10$^{-6}$ M) or an equivalent volume of sterile water (CO) was added. After 24 hr some [Met$^5$]-enkephalin-treated cultures continued to receive [Met$^5$]-enkephalin, whereas other [Met$^5$]-enkephalin-treated cultures received sterile water ([Met$^5$]-enkephalin-CO) Drugs and media were changed daily. Data represent means±SE for at least 2 aliquots/well from 2 wells/group/time point. The [Met$^5$]-enkephalin-CO group differed significantly from the [Met$^5$]-enkephalin group at $p<0.05(*)$ and $p<0.01(**)$.

The inhibitory effect of [Met$^5$]-enkephalin on cell number could be related to cytotoxicity, rather than a biological interaction of peptide on mechanisms of cell proliferation. To address the question of whether the effects of [Met$^5$]-enkephalin on cell number were permanent, a study was designed to determine if the inhibitory effects of [Met$^5$]-enkephalin could be reversed. Cultures of HT-29 cells were exposed for 24 hr to 10$^{-6}$ M [Met$^5$]-enkephalin and the number of peptide-treated cells was reduced 30% from control levels (FIG. 5). Twenty-four hr after the [Met$^5$]-enkephalin media was removed and replaced with control media the cultures contained 37% more cells than those continuing to receive [Met$^5$]-enkephalin. Forty-eight hr after removal of [Met$^5$]-enkephalin and replacement with control media, cell number was more than 80% greater than that of cultures maintained with [Met$^5$]-enkephalin. Calculation of the increase in number of cells per hour for the final 24 hours of the experiment revealed that in contrast to controls (8,917 cells/hr) cells initially exposed to [Met$^5$]-enkephalin and subsequently incubated in drug-free media grew at a rate of 12,917/hr. Cultures continuing to be maintained on [Met$^5$]-enkephalin (i.e. exposure to [Met$^5$]-enkephalin for a total of 72 hr), however, increased at a rate of 3,542 cells/hr during this period.

EXAMPLE E
Antibody Blockade of [Met$^5$]-Enkephalin Inhibition

Figure 6:
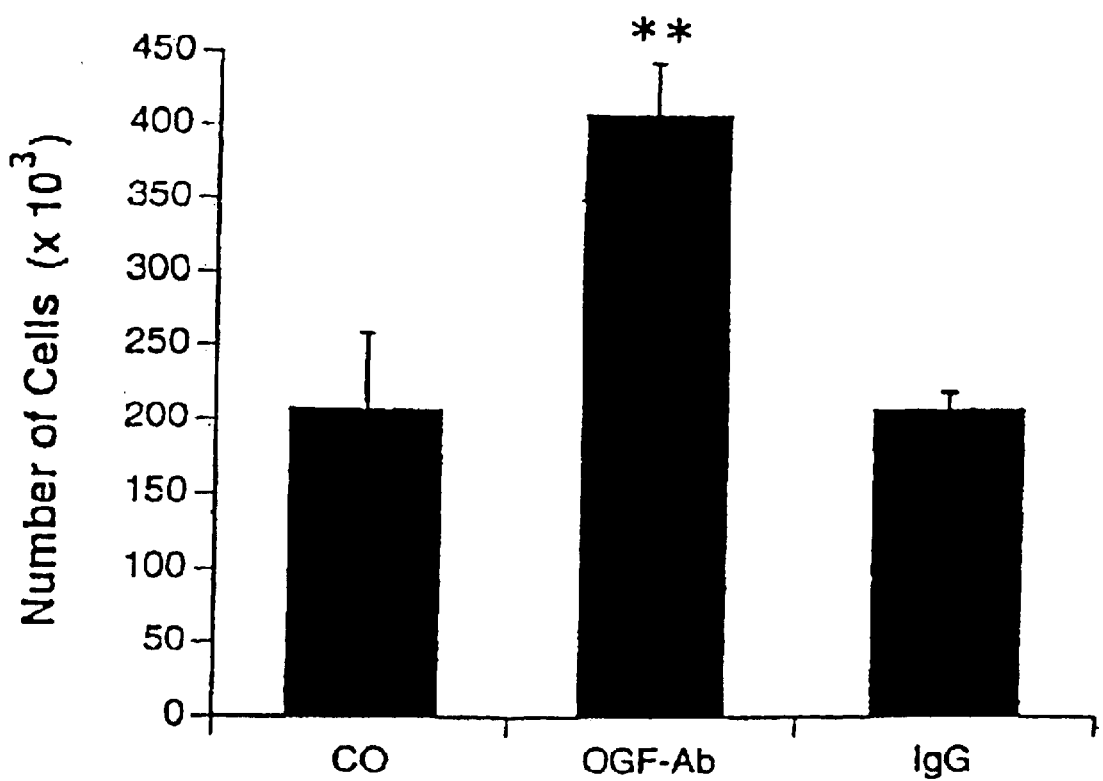
FIG. 6 graphically depicts cultures of HT-29 colon cells exposed to a polyclonal antibody to [Met$^5$]-enkephalin generated in rabbits ([Met$^5$]-enkephalin-Ab), non-immune rabbit immunoglobulin (IgG), or an equivalent volume of sterile water (CO) and examined 48 hr later; 4 samples per treatment were utilized. Cells were seeded and allowed to grow for 24 hr before antibody was added. Media and compounds were replaced daily. Data represent means±SE for at least 2 aliquots/well from 2 well/group/time point. Significantly different from CO and the non-immune IgG group at $p<0.01$ (**).

As [Met$^5$]-enkephalin is an inhibitory peptide that is tonically active in HT-29 cell cultures, then blockade of [Met$^5$]-enkephalin-receptor interaction with an antibody to [Met$^5$]-enkephalin will increase cell number (FIG. 6). Cultures of HT-29 treated with 1:1000 dilutions of anti-[Met$^5$]-enkephalin or non-immune rabbit IgG immunoglobulin (each culture received approximately 34 µg of antibody or IgG immunoglobulin) were counted 48 hr later. The number of cells in cultures treated with anti-[Met$^5$]-enkephalin was almost 2-fold greater than in control cultures, but no differences in cell number were noted between non-immune IgG-treated and control cultures.

Figure 7:
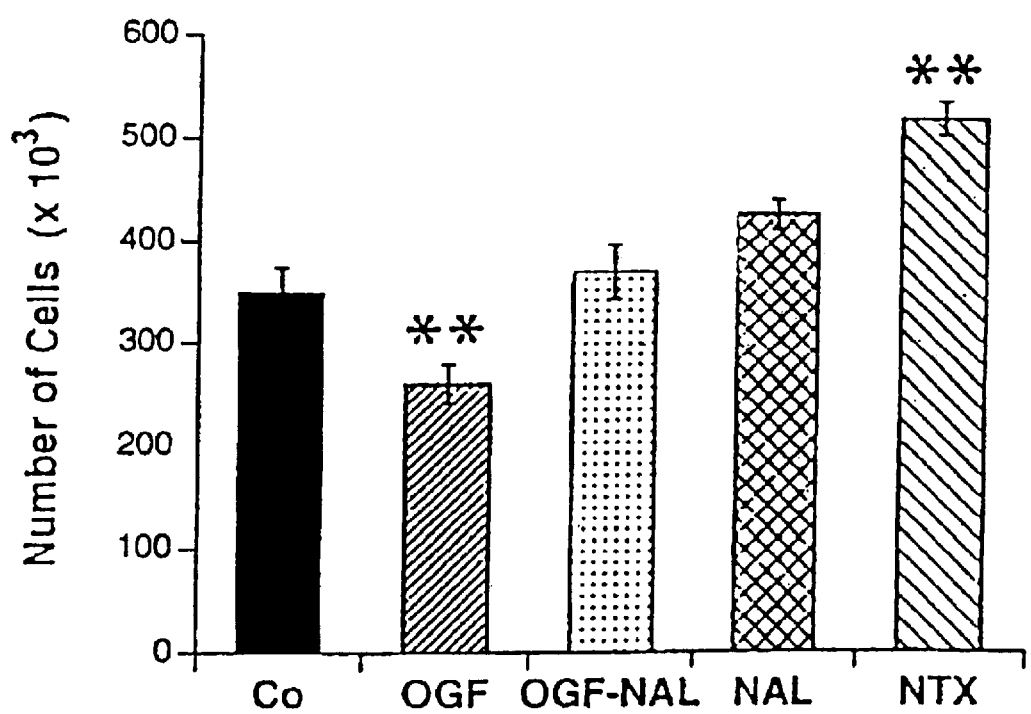
FIG. 7 graphically depicts the effects of [Met$^5$]-enkephalin and NTX on the number of HT-29 colon cancer cells grown in serum-free media after 48 hr. Twenty-four hr after the seeding of HT-29 cells acclimated to serum-free conditions, cultures were exposed to [Met$^5$]-enkephalin, [Met$^5$]-enkephalin and naloxone ([Met$^5$]-enkephalin-NAL), naloxone alone (NAL), or NTX at a concentration of 10$^{-6}$ M; media and compounds were changed daily. Data represents means±SE for at least 2 aliquots/well from 2 wells/group. Significantly different from controls at $p<005(*)$ and $p<0.01(**)$ FIG. 8 are photomicrographs of HT-29 colon cancer cells growing in culture for 3 days. Cultures were stained with hematoxylin and eosin (A) or antibodies to ([Met$^5$]-enkephalin (1:100) (B) or ζ-opioid receptor (D); rhodamine-conjugated immunoglobulin G (1:100) served as the secondary antibody. Note immunoreactivity in the cytoplasm of the opithelial cells (arrows); cell nuclei were not stained. No immunoreactivity was detected in preparations stained with antibodies preabsorbed with either the [Met$^5$]-enkephalin (C) or the 17 kDa polypeptide of the ζ-opioid receptor (E). Scale bar=75 μm.

EXAMPLE F
Opioid Peptide Modulation of HT-29 Colon Cancer Cells in Serum-free Media The experiments showing that opioid peptides, and in particular [Met$^5$]-enkephalin, influenced the growth of HT-29 human colon cancer cells were conducted in serum containing media. To eliminate any confounding variables introduced by the serum, HT-29 cells were adapted to grow in serum-free media and subjected to NTX or [Met$^5$]-enkephalin. Adaptation to conditions of serum-free media took place over a 4-week period by slowly reducing serum from 10%, 5%, 2.5%, 1.25% to 0%. Cells were plated (plating efficiency into serum-free-media was 43%–51%). in equal numbers and treated with 10$^{-6}$M concentrations of [Met$^5$]-enkephalin, [Met$^5$]-enkephalin and NAL, NAL or NTX. Cells were counted 48 hr (data not shown) and 72 hr later (FIG. 7). At both time points, [Met$^5$]-enkephalin had an inhibitory effect on cell growth in a receptor-mediated fashion, and NTX resulted in a significant increase in cell number.

EXAMPLE G
Opioid Peptides and the Growth of COLO 205 and WiDr Human Colon Cancer Cells To examine the ubiquity of opioid activity with respect to colon cancer, two other colon cancer cell lines were investigated: COLO 205 and WiDr. Administration of 10$^{-6}$ M NTX for 48 hr, with media and drug replaced after 24 hr, showed that NTX-treated cultures had 76% and 68% more COLO 205 and WiDr cells, respectively, than control cultures; these values were significantly different from control levels at p<0.01. In contrast, cultures of COLO 205 and WiDr cells subjected to 10$^{-6}$ M [Met$^5$]-enkephalin were subnormal in number, containing 58% ($p<0.01$) and 41% ($p<0.05$) cells, respectively, fewer cells than control cultures. The suppressive effects of [Met$^5$]-enkephalin on growth were eliminated by addition of $10^{-6}$ M naloxone; naloxone ($10^{-6}$ M) alone had no influence on growth.

EXAMPLE H

Immunocytochemical Detection of [Met$^5$]-Enkephalin and the ζ-Opioid Receptor

Figure 8A:
Figures 8B, 8C:
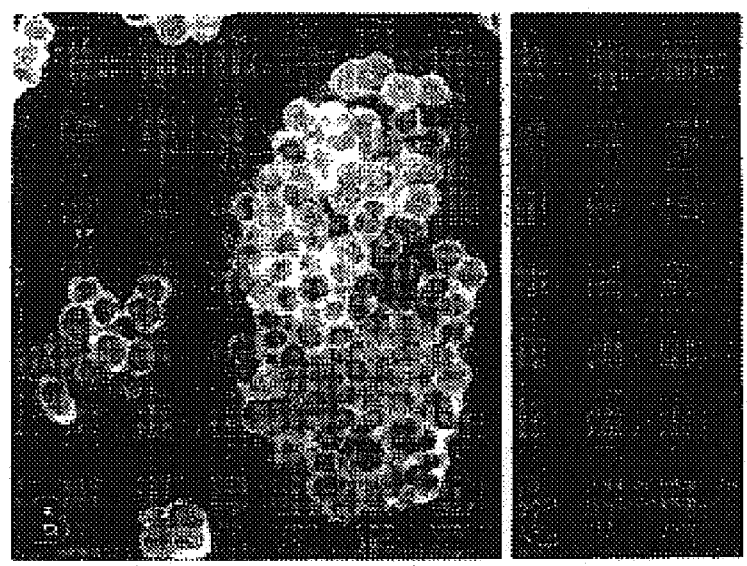
Figures 8D, 8E:
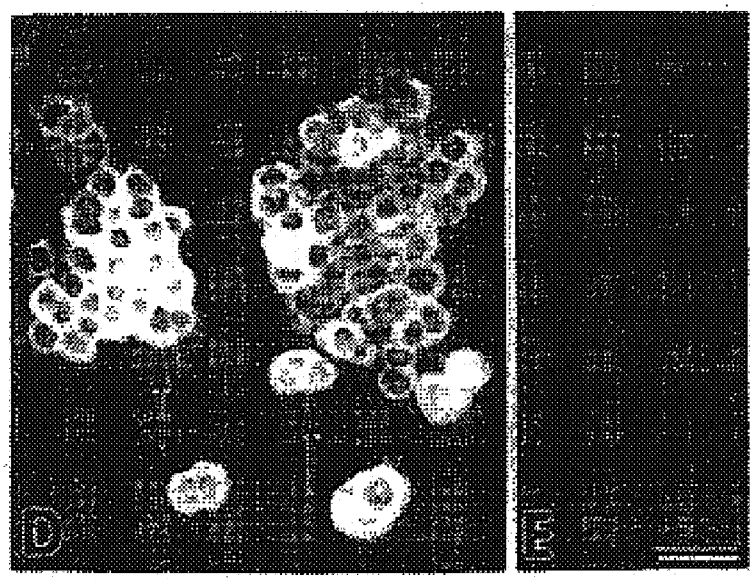

Antibodies to [Met$^5$]-enkephalin and to the ζ-opioid receptor were used with immunocytochemistry to determine the presence and location of this growth-related peptide and its receptor in HT-29 cells (FIG. 8). Both antibodies provided a similar pattern of immunocytochemical labeling in the cells (FIGS. 8B, 8D). The cytoplasm, but not the nuclei, of the HT-29 cells was immunofluorescent. No staining was recorded in control specimens processed with antibody preabsorbed with respective antigens (FIGS. 8C, 8E) or in samples incubated with secondary antibody only.

EXAMPLE I

Receptor Binding Assays and Receptor Regulation

Although the ζ-opioid receptor was associated with HT-29 colon cancer cells by immunocytochemistry, the characteristics of this receptor required definition. In preliminary studies optimal conditions of binding were defined and all parameters (i.e., temperature, pH, protein concentration, protease inhibitors) but the time of incubation (90 min of HT-29 cells in vitro and 150 min for in vivo preparations) were similar for HT-29 cells in culture and in xenografts. Binding of [$^3$H]-[Met$^5$]-enkephalin to nuclear preparation of HT-29 cells from culture was specific and saturable, and a one-site model of kinetics was determined by computer analysis; a binding affinity ($K_d$) of 8.9 nM and a binding capacity ($B_{max}$) of 43 fmol/mg protein recorded (FIG. 9).

In order to begin to evaluate the regulation of the [Met$_5$]-enkephalin receptor, the regulatory properties of [$_3$H]-[Met$_5$]-enkephalin binding in colon cancer cells were examined. HT-29 cells subjected to an opioid receptor blockade (i.e., NTX) for 48 hr had a $K_d$ and $B_{max}$ similar to control cells in culture. In the case of chronic exposure to [Met$^5$]-enkephalin, the HT-29 cells had a $K_d$ comparable to that of control cells, but the $B_{max}$ was reduced by 50% (Table 2).

TABLE 2

$K_d$ and $B_{max}$ of [3H]-[Met$^5$]-enkephalin on HT-29 human colon cells after 48 h of exposure to OGF or NTX

| Treatment | $K_d$ | $B_{max}$ |
|---|---|---|
| Control | 4.2 ± 0.7 | 37.6 ± 4.4 |
| NTX | 4.3 ± 0.1 | 38.8 ± 1.7 |
| OGF | 1.9 ± 1.1 | 18.6 ± 1.1* |

Data represent means ± SE. $K_d$, binding affinity; $B_{max}$, binding capacity; NTX, naltrexone; OGF, opioid growth factor. *Significantly different from controls at $P < 0.01$.

EXAMPLE J

Presence and Autocrine Production of [Met$^5$]-Enkephalin

Figure 10:
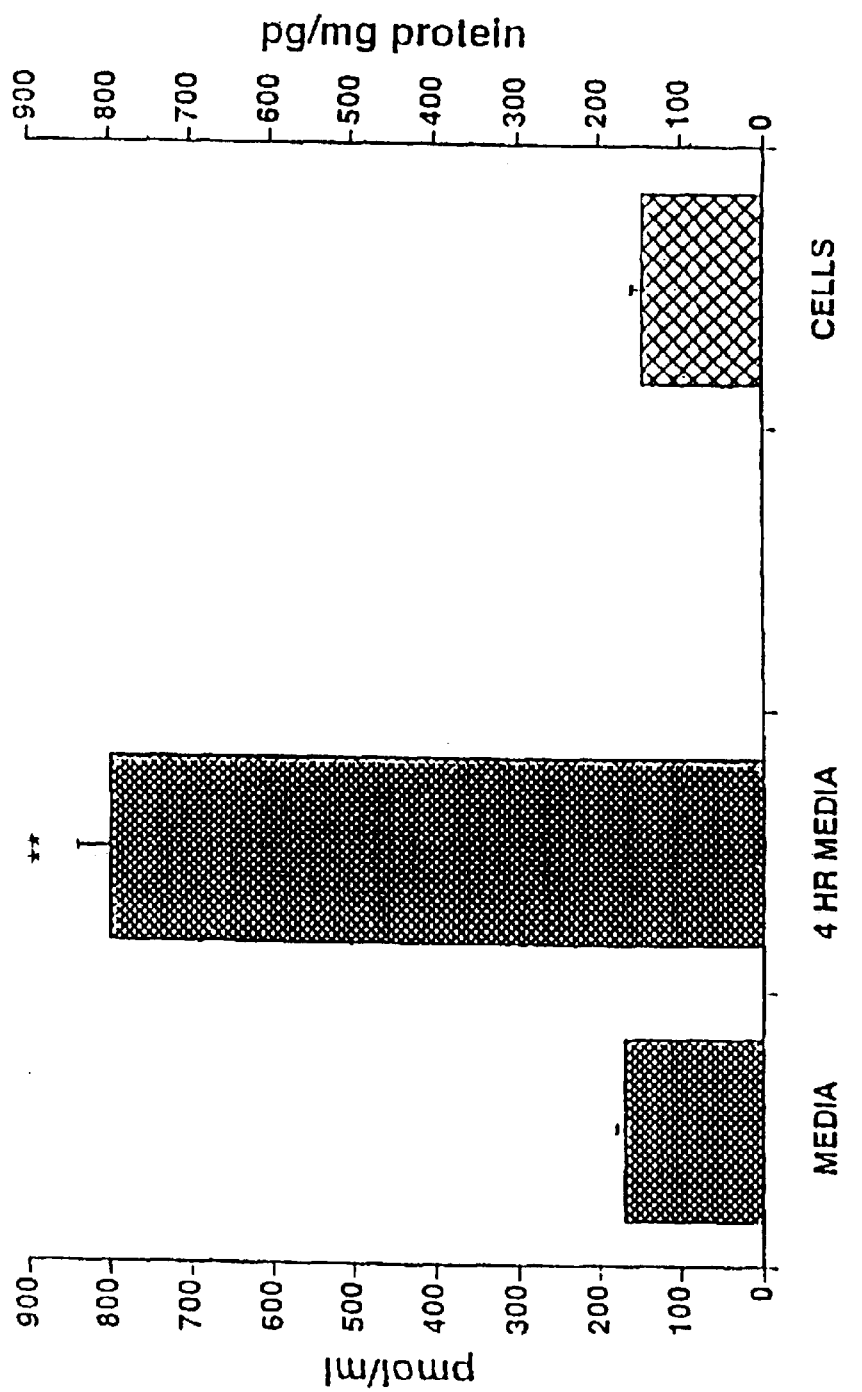
FIG. 10 graphically depicts [Met$^5$]-enkephalin levels as detected by radioimmunoassay in fresh media (media), media collected 4 hr after addition to log phase cultures of HT-29 colon cancer cells, and in HT-29 cells harvested in log phase. Media at 4 hr had 4.7-fold higher levels of [Met$^5$]-enkephalin; this difference was statistically significant ($p<0.01$). Data represent means±SE for 4 separate experiments.

Radioimmunoassay of the [Met$^5$]-enkephalin in HT-29 cultures showed that the cells had 145.0±12.6 pg of [Met$^5$]-enkephalin/mg protein (FIG. 10). In contrast to fresh media (168.8±9.7 μmol/ml), media from cells incubated for 4 hr had 4.8-fold more [Met$^5$]-enkephalin (FIG. 10).

EXAMPLE K

Characterization of [$^3$H]-[Met$^5$]-Enkephalin Binding

Figure 11:
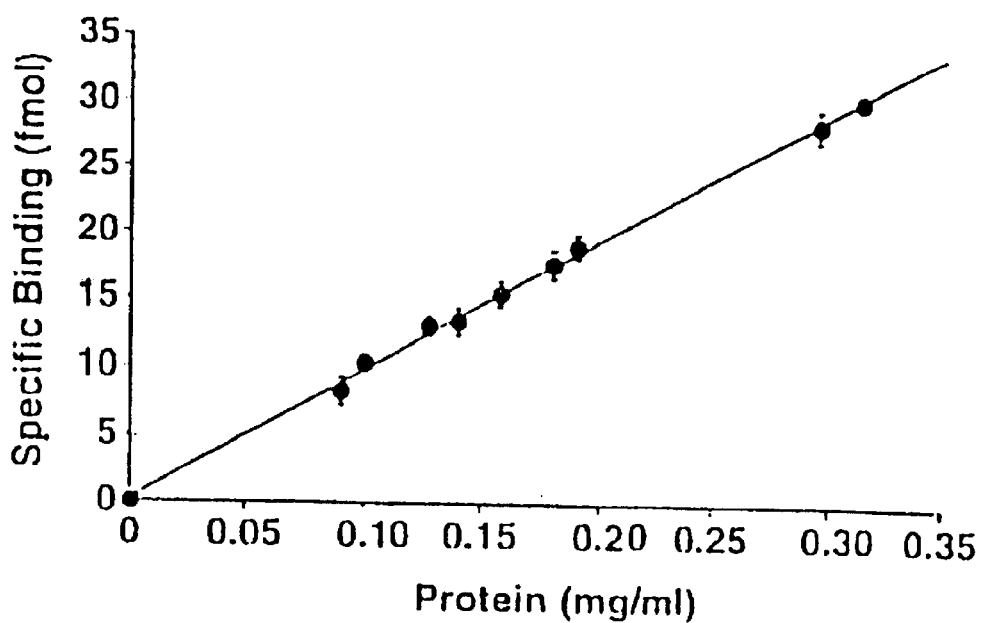
FIG. 11 graphically depicts dependence of HT-29 nuclear homogenate protein concentration on binding of [$^3$H]-[Met$^5$]-enkephalin. Increasing concentration of protein were incubated with 4 nM [$^3$H]-[Met$^5$]-enkephalin in the presence or absence of 100 nM unlabeled [Met$^5$]-enkephalin for 150 minutes at 4° C. at pH 7.4. Values are means±SE for at least 2 experiments performed in duplicate.
Figure 12:
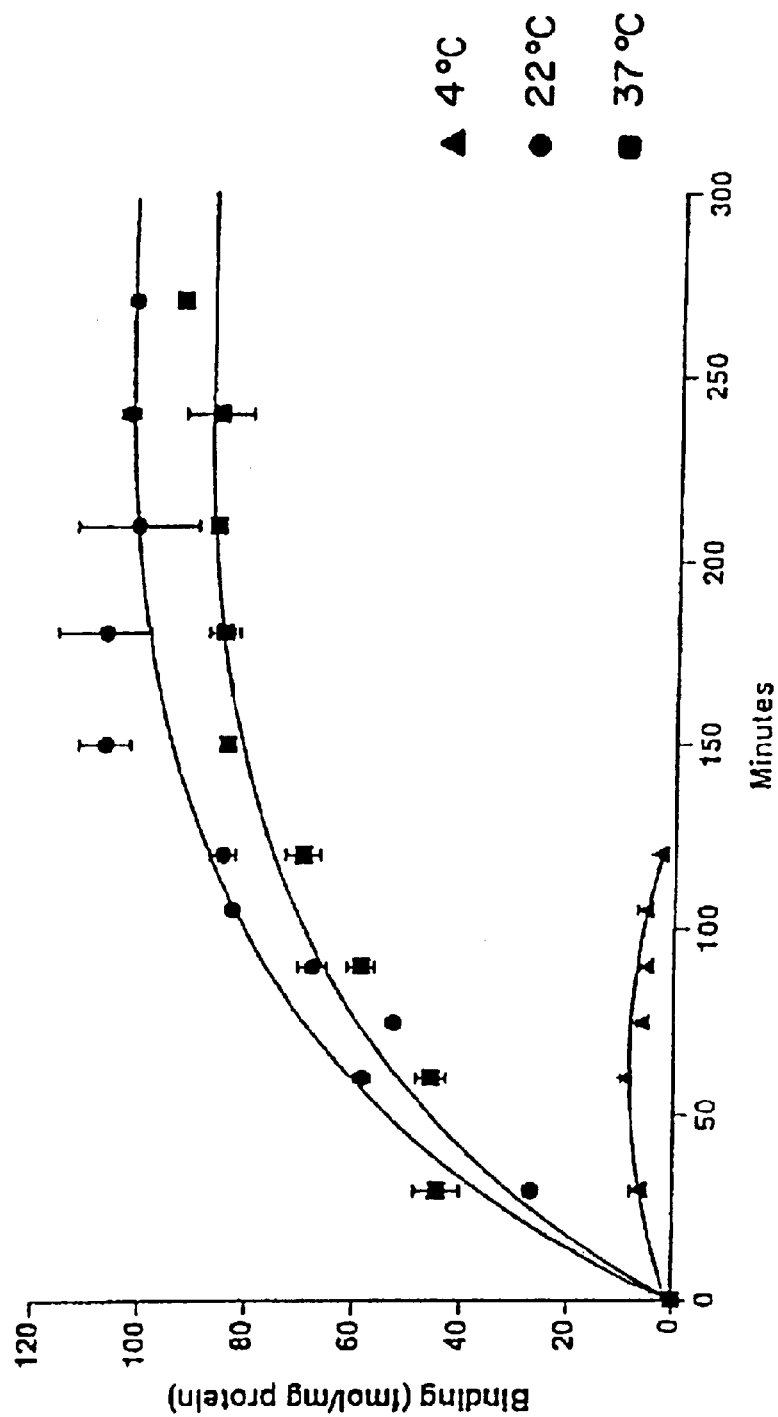
FIG. 12 graphically depicts dependence of [$^3$H]-[Met$^5$]-enkephalin binding to HT-29 nuclear homogenates on time and temperature of incubation. Homogenate protein was incubated with 4 nM [$^3$H]-[Met$^5$]-enkephalin in the presence or absence of unlabeled [Met5]-enkephalin (for nonspecific binding) at either 4, 22 or 37° C. for varying periods of time. Data are mean values±SE for at least 3 experiments performed in duplicate.
Figure 13:
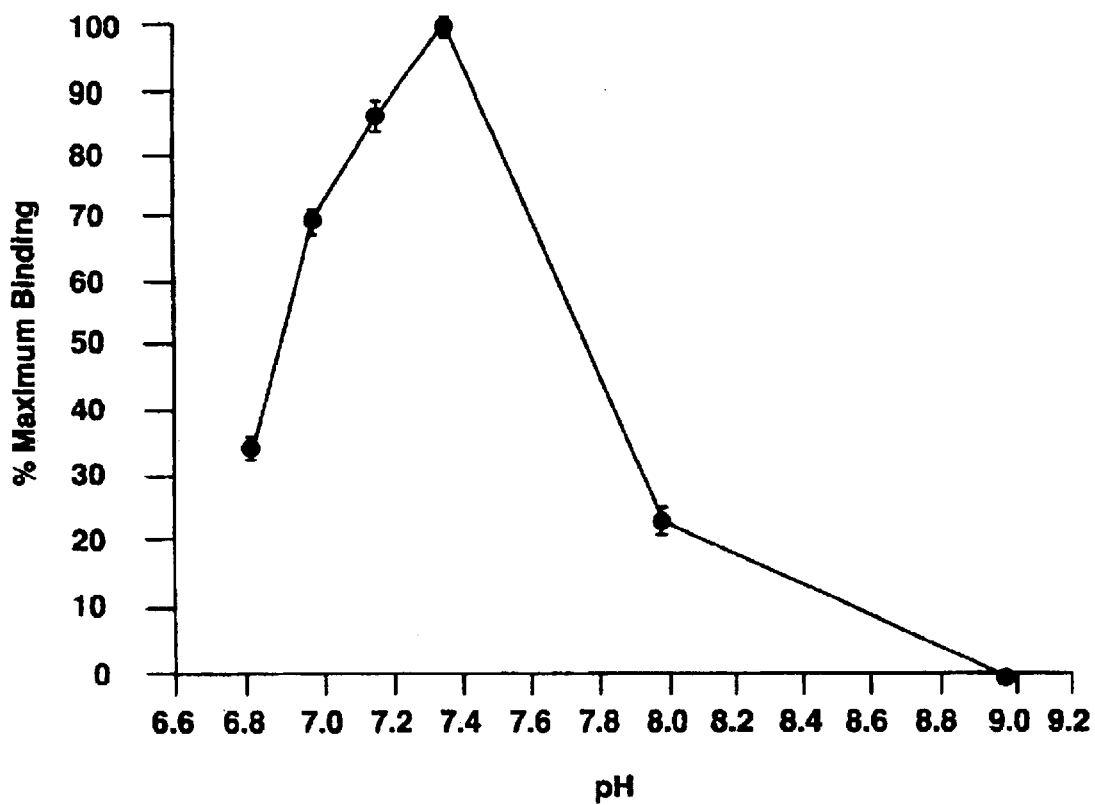
FIG. 13 graphically depicts dependence of [$^3$H]-[Met$^5$]-enkephalin binding to HT-29 nuclear homogenates on pH. Homogenate protein was incubated with 4 nM [$^3$H]-[Met$^5$]-enkephalin in the presence or absence of unlabeled [Met5]-enkephalin (for nonspecific binding) at 22° C. at a variety of pH levels. A pH of 7.4 was found to be optimal.

The optimal conditions for binding of [$^3$H]-[Met$^5$]-enkephalin to HT-29 nuclear (P1) homogenates were determined. Using tumor tissue obtained from nude mice, specific binding of [$^3$H]-[Met$^5$]-enkephalin to HT-29 nuclear homogenates was dependent on protein concentration and was linear between 95 and 320 μg/ml (FIG. 11). Protein concentrations greater than 350 μg/ml tended to clog the glass fiber filters, resulting in high background and unreliable data. Binding of [$^3$H]-[Met$^5$]-enkephalin to HT-29 P1 homogenates was also dependent on time and temperature (FIG. 12). Maximum specific binding occurred at 22° C., reaching equilibrium at 150 minutes. Binding at 4° C. and 37° C. was 2.8% and 78%, respectively, of the binding at 22° C. The binding of radiolabeled [Met$^5$]-enkephalin to HT-29 nuclear homogenates was also dependent on pH, with an optimal pH recorded at 7.4 (FIG. 13).

Figure 14:
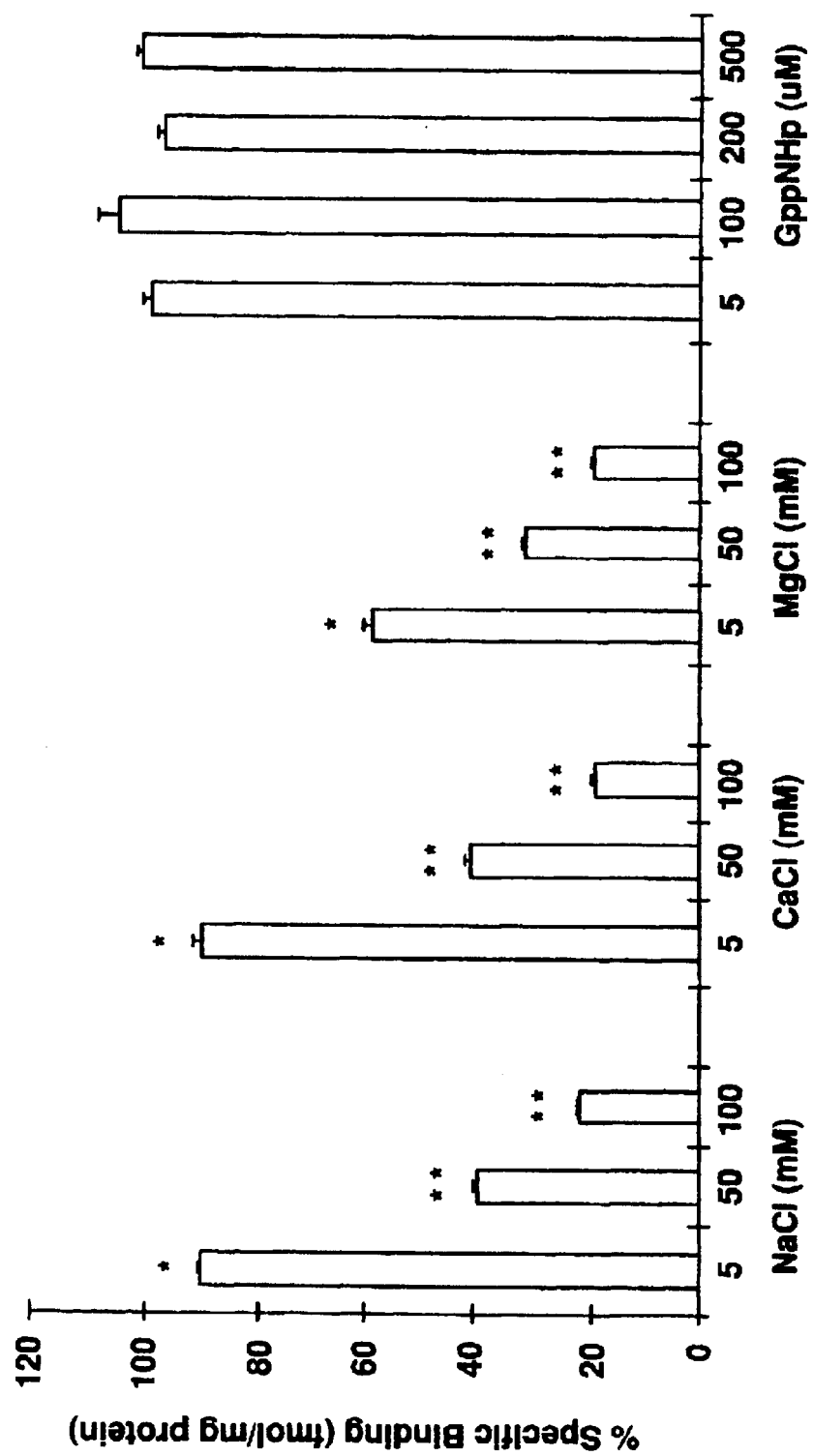
FIG. 14 graphically depicts the effect of cations and guanyl nucleotides on the binding of [$^3$H]-[Met$^5$]-enkephalin (4 nM) to HT-29 nuclear homogenates. Histograms represent the percent of specific binding±SE. Significantly different from the controls at $p<0.05(*)$ and $p<0.01$ (**)

The effects of monovalent and divalent cations on [$^3$H]-[Met$^5$]-enkephalin binding to HT-29 nuclear homogenates are presented in FIG. 14. NaCl, CaCl$_2$, and MgCl$_2$ at concentrations of 5, 50, and 100 mM reduced specific [$^3$H]-[Met$^5$]-enkephalin binding by as much as 82%. The binding of [$^3$H]-[Met$^5$]-enkephalin was not markedly reduced by addition of 5, 100, 200, or 500 μM concentrations of GppNHp to the binding assays. Competition experiments using 4 nM [$^3$H]-[Met$^5$]-enkephalin and a range of opioid and non-opioid antagonists and agonists were performed to examine the specificity and relationship of radiolabeled [Met$^5$]-enkephalin to its binding site (FIG. 16).

Figure 15:
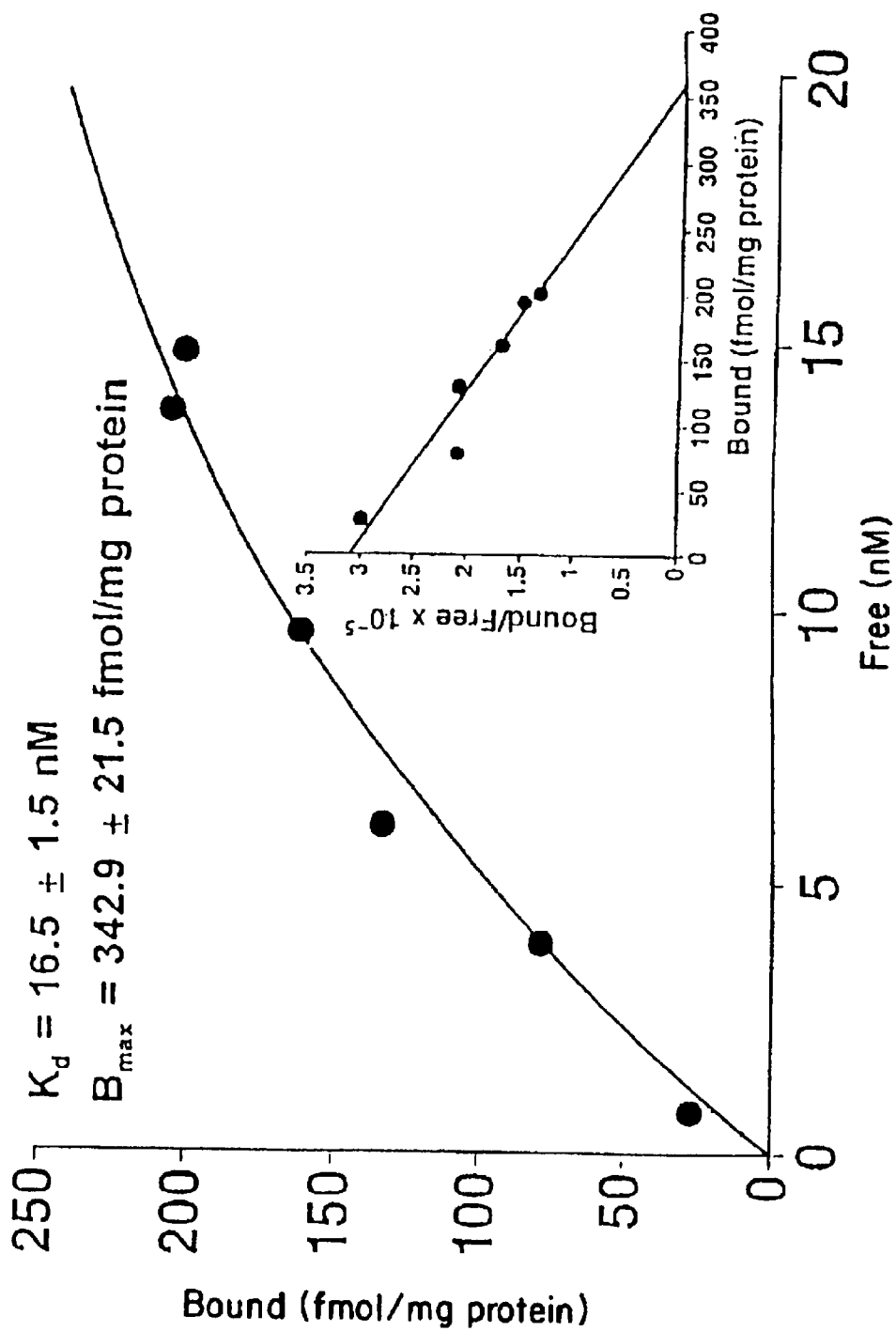
FIG. 15 graphically depicts representative saturation isotherm of specific binding of [$^3$H]-[Met$^5$]-enkephalin to HT-29 nuclear homogenates. Mean±SE binding affinity ($K_d$) and maximal binding capacity ($B_{max}$) values from 16 experiments performed in duplicate are shown. Representative Scatchard plot (inset) of specific binding of radiolabeled [Met$^5$]-enkephalin to HT-29 nuclear homogenates revealed a one-site model of binding.

Utilizing the optimal conditions for protein concentration (120–240 μg/ml), time (150 min), temperature (22° C.), and pH (7.4) described above, in a buffer containing 50 mM Tris-HCl, 0.1 mg/ml bacitracin, 1 μg/ml leupeptin, 6 nM thiorphan, 1 mM EGTA, and 0.6 mg/l PMSF, [$^3$H]-[Met$^5$]-enkephalin binding to HT-29 homogenates (P1 fraction) was found to be specific and saturable (FIG. 15). Computer analysis of binding showed the data best fit a one-site model with an average equilibrium dissociation constant $K_d$ of 15.4±2.0 nM and a mean binding capacity (Bmax) of 364.8±25.7 fmol/mg protein.

Figure 16:
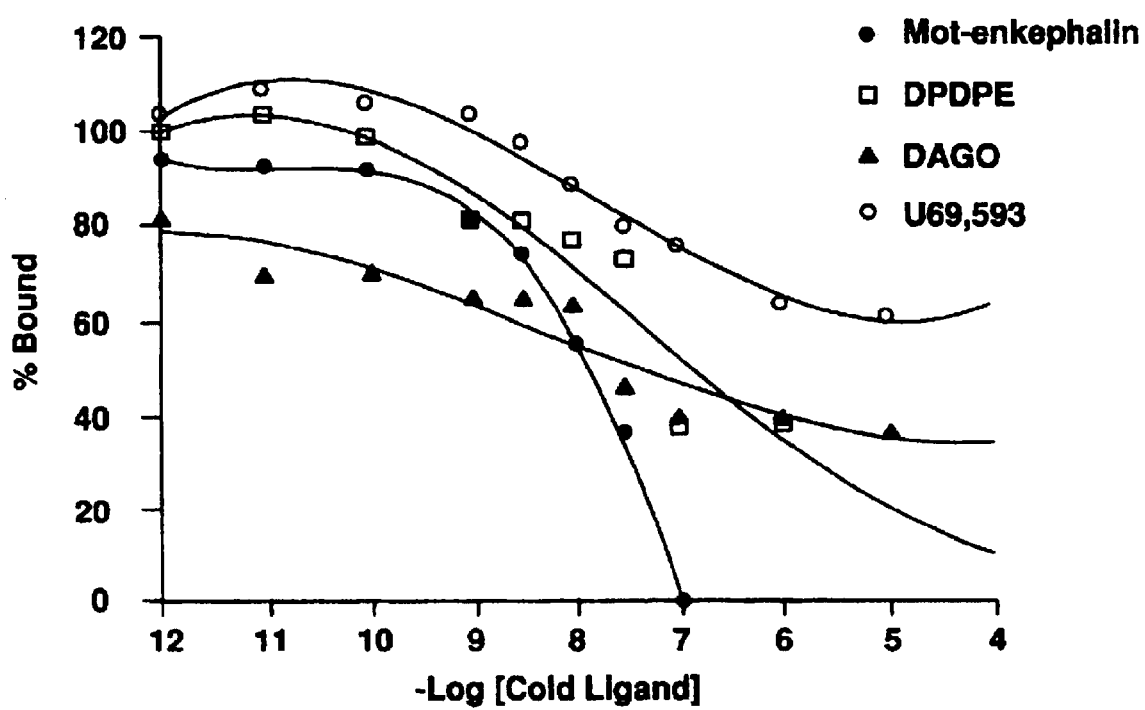
FIG. 16 graphically depicts competition binding assays were performed by incubating 4 nM [$^3$H]-[Met$^5$]-enkephalin with varying concentration ($10^{-12}$ to $10^{-5}$ M) of unlabeled [Met$^5$]-enkephalin, DAGO, DPDPE, or U69,593 using nuclear homogenates of HT-29 human colon tumors. Maximum specific binding is plotted as a percentage of total binding.

Table 3 and FIG. 16 present the results of these studies. [Met$^5$]-enkephalin exhibited the greatest potency of any of the 19 compounds tested, having a 2.3-fold greater ability to displace [$^3$H]-[Met$^5$]-enkephalin than the next ranking compound (i.e., [Met$^5$]-enkephalin-Arg$^6$-Gly$^7$-Leu$^8$). The binding site recognized the opioid antagonists (−)-naloxone and naltrexone. Competition studies also showed that this binding site distinguished stereoisomers, with (−)-naloxone being 100,000-fold more potent than (+)-naloxone in displacing [$^3$H]-[Met$^5$]-enkephalin. Ligands related to the μ receptor (DAMGO, morphine) required about 3-fold more peptide than [Met$^5$]-enkephalin to displace [$^3$H]-[Met$^5$]-enkephalin. Compounds related to the delta receptor and epsilon receptor, such as DPDPE and β-endorphin, were 6.0- and 4.3-fold, respectively, less potent than [Met$^5$]-enkephalin in displacing radiolabeled [Met$^5$]-enkephalin binding. Compounds related to the kappa opioid receptor (EKC, U69,593, dynorphin A 1–8) and sigma receptor (SKF-10,047) were not competitive in displacing [$^3$H]-[Met$^5$]-enkephalin binding. The gastrointestinal hormones gastrin and CCK-8 exhibit ability to compete with radiolabeled [Met⁵]-enkephalin, while their antagonists (L365,260, L364,718) were not very competitive. The gastrointestinal hormone somatostatin displayed little activity in displacing [$^3$H]-[Met⁵]-enkephalin. Subcellular fractionation studies. Sucrose gradient centrifugation was performed to separate the nuclear (P1), membrane (P2), microsomal (P3), and soluble (S3) fractions. In these experiments, specific and saturable binding of [$^3$H]-[Met⁵]-enkephalin was detected in the P1 fraction, and computer analysis revealed a one-site model of binding with a $K_d$ of 6.6±0.2 nM and $B_{max}$ of 256.0±12.6 fmol/mg protein (Table 4). No specific and saturable binding of [$^3$H]-[Met⁵]-enkephalin was found in the P2, P3, or S3 fractions.

TABLE 3

Potency of opioid and nonopioid ligands to compete for binding of [$^3$H][Met⁵]enkephalin (4.0 nM) in nuclear homogenates of HT-29 human colon tumors

| Ligand | IC$_{50}$, nM | K$_I$ nM |
|---|---|---|
| [Met⁵]enkephalin | 16.5 ± 1.5 | 12.7 ± 1.2 |
| [Met⁵]enkephalin-Arg⁶-Gly⁷-Leu⁸ | 37.5 ± 7.5 | 28.9 ± 5.8 |
| DAMGO | 42.5 ± 0.5 | 32.7 ± 0.4 |
| Morphine sulfate | 45.0 ± 3.0 | 34.5 ± 2.5 |
| β-Endorphin | 71.0 ± 6.0 | 54.6 ± 4.6 |
| [Leu⁵]enkephalin | 75.0 ± 5.0 | 57.7 ± 3.9 |
| Gastrin | 77.5 ± 7.5 | 59.6 ± 5.8 |
| Naltrexone hydrochloride | 90.5 ± 3.5 | 69.6 ± 2.7 |
| DPDPE | 95.0 ± 5.0 | 73.1 ± 3.9 |
| CCK-8 | 103 ± 2 | 79.0 ± 2.0 |
| (−)-Naloxonehydrochloride | 115 ± 5 | 88.5 ± 3.9 |
| Dynorphin A-(1–8) | 375 ± 25 | 289 ± 20 |
| SKF-10047 | 795 ± 5 | 612 ± 4 |
| L-365260 | 1,250 ± 250 | 960 ± 190 |
| (+)-Naloxone hydrochloride | >10⁻⁵M | >10⁻⁵M |
| Somatostatin | >10⁻⁵M | >10⁻⁵M |
| L-364718 | >10⁻⁵M | >10⁻⁵M |
| U-69593 | >10⁻⁴M | >10⁻⁴M |
| EKC | >10⁻²M | >10⁻²M |

Data represent means ± SE from at least 2 independent assays. Equilibrium dissociation constant for [Met⁵]-enkephalin was 15.4 ± 2.0 nM. IC$_{50}$, concentration that inhibits 50% of maximal response; K$_I$, inhibition constant; DAMGO, [D-Ala²,N-Me-Phe⁴,Gly⁵-ol]enkephalin; DPDPE, (D-Pen², Pen⁵]enkephalin; CCK-8, cholecystokinin octapeptide; EKC, ethylketocyclazocine

TABLE 4

Subcellular fractionation studies utilizing [$^3$H][Met⁵]enkephalin and HT-29 human colon tumors

| Fraction | Cellular Composition | K$_d$, nM | B$_{max}$, fmol/mg protein |
|---|---|---|---|
| P$_1$ | Nuclear | 6.6 ± 0.2 | 256.0 ± 12.6 |
| P$_2$ | Membranes | * | * |
| P$_3$ | Microsomal | * | * |
| S$_3$ | Soluble | * | * |

Data represent means ± SE for independent assays. K$_d$, dissociation constant; B$_{max}$, maximal binding capacity. *No specific or saturable binding.

Binding studies utilizing radiolabeled ligands for the $\mu$, $\delta$ and $\kappa$ opioid receptors were performed on both P1 and P2 homogenates of HT-29 tumors (Table 5). Specific and saturable binding of [$^3$H]-DAMGO, [$^3$H]-DPDPE, or [3H]-U69,593 was detected in the P2 fraction for each ligand with a K$_d$ ranging from 2.0 to 12.8 nM, and a B$_{max}$ ranging from 9.8 to 20.9 fmol/mg protein. Specific and saturable binding was not detected in the P1 fraction for any of these ligands.

[$^3$H]-[Met⁵]-enkephalin binding to fresh human colon tumor homogenates. Human colon tumors were obtained from surgical resections and binding studies utilizing radio= labeled [Met⁵]-enkephalin were performed on P1 homogenates (Table 6).

TABLE 5

Binding of HT-29 nuclear (P$_1$) and membrane (P$_2$) homogenates to radiolabeled ligands selective for $\mu$-, $\delta$-, and $\kappa$-opioid receptors

| Ligand | Receptor | Fraction | K$_d$, nM | B$_{max}$, fmol/mg protein |
|---|---|---|---|---|
| [3H]DAMGO | $\mu$ | P1 | * | * |
| | | P2 | 12.8 ± 4.5 | 20.9 ± 4.8 |
| [3H]DPDPE | $\delta$ | P1 | * | * |
| | | P2 | 2.6 ± 1.2 | 9.8 ± 4.8 |
| [3H]U-69593 | $\kappa$ | P1 | * | * |
| | | P2 | 2.0 ± 0.5 | 13.9 ± 1.5 |

Data represent means ± SE for 2 independent assays. *No specific or saturable binding.

TABLE 6

Binding of [$^3$H][Met⁵]enkephalin to nuclear homogenates of fresh human colon tumors

| Patient | Age, yr | Sex | Tumor Type | K$_d$, nM | B$_{max}$, fmol/mg protein |
|---|---|---|---|---|---|
| 1 | 77 | M | Splenic flexure adenocarcinoma (moderately differentiated) | 15.7 ± 6.7 | 34.3 ± 9.0 |
| 2 | 72 | F | Sigmoid adenocarcinoma (moderately differentiated) | 6.7 ± 0.5 | 32.7 ± 1.4 |

Data represent means ± SE from at least 2 assays (each performed in duplicate).

[$^3$H]-[Met⁵]-enkephalin binding to human colon tumor homogenates was found to be specific and saturable. Computer analysis of binding showed the data to best fit a one-site model, with an equilibrium dissociation constant (K$_d$) of 11.2±3.6 nM and a mean binding capacity (B$_{max}$) of 33.5±4.1 fmol/mg protein recorded when data from both patients were averaged.

The [Met⁵]-enkephalin, depressed growth of HT-29 human colon cancer cells from 17% to 41% at 12 to 72 hr after administration of 10⁻⁶ M concentration; consistent with previously defined nomenclature, this peptide was termed opioid growth factor ([Met⁵]-enkephalin). [Met⁵]-enkephalin action exhibited a dose-response relationship, was reversible and not cytotoxic, and opioid receptor mediated. Growth inhibition by [Met⁵]-enkephalin was not dependent on serum, and was noted in the two other human colon cancer cell lines examined: WiDr and COLO 205. This peptide continually repressed growth because an increase in cell number was noted when cells were exposed to the potent opioid antagonist naltrexone or an antibody to [Met⁵]-enkephalin. Both [Met⁵]-enkephalin and its receptor, zeta ($\zeta$), were found in colon cancer cells by immunocytochemistry, and receptor binding assays revealed a nuclear associated receptor with a K$_d$ of 8.9 nM and a B$_{max}$ of 43 fmol/mg of protein. [Met⁵]-enkephalin was produced and secreted by the tumor cells. [Met⁵]-enkephalin has a direct, tonic, inhibitory action on the growth of human colon cancer cells and contributes to our understanding of the mechanisms underlying the marked anti-tumor effect of this peptide in nude mice inoculated with human colon cancer cells.

EXAMPLE 2

[MET⁵]-Enkephalin Inhibits Pancreatic Cancer 2-1. Animals and Tumors

BxPC-3 human pancreatic cancer cells, purchased from the American Type Culture Collection (Rockville, Md.), were grown in RPMI media containing 10% fetal calf serum, penicillin (10 units/ml), and streptomycin (100 µg/ml) in an atmosphere of 93% air and 7% $CO_2$ at 37° C. Cell viability was determined by the trypan blue exclusion test. Three-to-4-week-old male athymic nude mice, obtained from Charles River Laboratories (Wilmington, Mass.), were injected subcutaneously over the right shoulder with BxPC-3 cells (log phase) in a 0.5 ml suspension of RPMI media. The day of tumor cell inoculation was considered day 0. Mice were evaluated daily and the date that the tumor became 'visible' was recorded. Individual tumors were measured with vernier calipers every 2 days. Measurements of the largest perpendicular dimensions were recorded and tumor volume was calculated using the formula: length×width$^2$×0.5[25]. The time of 'initial' appearance of a tumor wag considered to be the day when tumor volume was 5 mm$^3$ of greater. All mice were euthanized and necropsied 30 days after tumor cell inoculation. Tumor tissues for receptor binding assays, radioimmunoassays, and immunocytochemistry were rapidly frozen in liquid nitrogen and stored at −70° C. until assayed. Blood was obtained from the inferior vena cava of each mouse, centrifuged in EDTA-coated tubes, and plasma was frozen for radioimmunoassay.

2-2. Tumor Incidence and Burden

In order to establish the appropriate number of cells required to produce tumors, groups of mice (4–5 animals each) were injected with either 0.1×10$^6$, 0.5×10$^6$, or 1×10$^6$, BxPC-3 cells. Latencies for the appearance of a visible tumor and initial tumor appearance were noted. The number of cells for inoculation in subsequent studies was selected as the lowest number of cells that produced 90% or more tumors with a latency of 5 or more days.

2-3. Drugs and Drug Treatment

Drug treatment was initiated on the day of tumor cell inoculation. Mice received subcutaneous injections three times daily (i.e. 0730, 1200,1700 h) of either 5 mg/kg [Met$^5$]enkephalin (OGF) or an equal volume of sterile water (controls); the dosage of OGF was not toxic. Injections were administered in the right or left flank. Animals were weighed weekly and appropriate dosage adjustments made.

The latencies for visible and initial tumor appearance, as well as the appearance of a tumor volume measuring 62.5 mm$^3$ (when each perpendicular measurement was 5 mm), were recorded.

2-4. Receptor Binding Assays

Receptor binding assays were performed according to procedures reported elsewhere [8] with some slight modifications. Briefly, nuclear homogenates were incubated for 150 min at 22° C. with [$^3$H-Met]enkephalin in the presence or absence of 100 nM unlabeled [Met$^5$]enkephalin. Six assays were performed to establish binding kinetics in control tumor tissue, whereas three independent assays were conducted on tumors from mice for comparison of OGF and control groups.

2-5. Radioimmunoassays of [Met ]Enkephalin

Radioimmunoassays were utilized to examine the presence and concentration of [Met]enkephalin in plasma and tumor tissue. Peptide was extracted from the plasma and tissue following instructions provided by the supplier, and [Met$^5$]enkephalin levels were determined with reagent kits from IncStar Corporation (Stillwater, Minn.). Specificity of the assay was 100% activity for [Met$^5$]enkephalin and a cross-reactivity of 2.8% with [Leu$^5$]enkephalin, 0.1% with α-endorphin (β-lipotropin 61–77), and less than 0.002% with β-endorphin, α-neoendorphin, substance P, and porcine dynorphin 1–13.

2-6. Immunocytochemistry

To examine for the presence of OGF and the ζ-opioid receptor, BxPC-3 tumors were removed from nude mice after 30 days, and frozen in isopentane and dry ice. Ten micron sections were collected on gelatin-coated slides, fixed in 95% acetone and permeabilized in 100% ethanol at −20° C., and blocked with Sorenson's phosphate buffer (SPB), 3% normal goat serum and 0.1% Triton X-100 at room temperature for 15 min. Tissues were processed for immunocytochemistry as described previously. In brief, specimens were incubated for 18 hr with either anti [Met$^5$] enkephalin IgG (1:150 dilution) or anti-ζ opioid receptor IgG (1:150 dilution) in SPB with 1% normal goat serum in 0.1% Triton X-100 in a humidified chamber at 4° C. Details about the production and characteristics of the polyclonal antibodies to [Met$^5$]enkephalin(CO-172) and ζ-receptor (AO-440) have been reported elsewhere. Sections were washed, and incubated for 45 min with rhodamine-conjugated goat anti-rabbit IgG (1:100) as the secondary antibody. Control slides included tissues stained with antibodies preabsorbed with the appropriate antigen or only secondary antibody. Specimens were examined using an Olympus microscope equipped with fluorescence optics.

2-7. Statistical Analysis

Latencies for visible and initial appearance as well as tumors ≧62.5 mm were analyzed using one way analysis of variance; subsequent comparisons were made with the Newman-Keuls tests. The number of mice with initial tumor appearance on selected days was expressed as a ratio of the total number of mice in the group, and comparisons of percentages were made with chi-square tests.

Receptor binding data were analyzed with a Lundon 1 (Saturation Isotherm Binding Analysis) computer program (Lundon Software, Chagrin Falls, Ohio) and Prism Software (San Diego, Calif.). Both analyses utilized non-linear least-squares regression. Saturation curves and Scatchard plots were computed directly by these programs.

Mean binding affinities and capacities for tumor tissue from animals in the OGF and control groups were compared using analysis of variance and Newman-Keuls tests.

Data from radioimmunoassays were evaluated by analysis of variance and Newman-Keuls tests.

2-8. Establishment of Tumor Burden

Three different quantities of BxPC-3 cells were injected into nude mice and the latencies and incidence of tumor appearance were recorded (Table 7). The latency for the appearance of a visible tumor ranged from 2.2 days to 4.1 days. The latency for initial tumor appearance ranged from 3 days to 6 days, with mice receiving the least amount of cells (i.e. 0.1×10$^6$) having the longest interval between tumor cell inoculation and detection of a measurable tumor. Within 3 days of tumor cell inoculation, 86% of mice receiving 0.5×10$^6$ cells and 88% of mice receiving 1×10$^6$ cells had tumors of ≧5 mm$^3$ in size; no mice receiving 0.1×10$^6$ cells had a tumor of this size. Seven days after tumor cell inoculation, all mice injected with 0.1×10$^6$ or 1×10$^6$ cells, and 13 of 14 mice receiving 0.5×10$^6$ cells, displayed a tumor of ≧5 mm$^3$. Based on these data, and our criterion of 90% tumor take with a latency of 5 or more days, 0.1×10$^6$ cells were inoculated into each mouse in all further studies.

TABLE 7

Tumor Formation and Incidence in Nude Mice
Inoculated with BxPC-3 Human Pancreatic Tumor Cells

| | Tumor Cell Member | | |
|---|---|---|---|
| | $0.1 \times 10^6$ | $0.5 \times 10^6$ | $1.0 \times 10^6$ |
| Latency (days) for visible tumor appearance[a] | 3.0 ± 0.0 | 4.1 ± 2.0 | 2.2 ± 0.1 |
| Latency (days) for initial tumor appearance[a] | 6.0 ± 0.4 | 5.1 ± 1.9 | 3.2 ± 0.1 |
| Number of mice with tumors of ≧ 5 mm³ 3 days after cell inoculation | 0/4 | 12/14 | 23/26 |
| Number of mice with tumors of ≧ 5 mm³ 7 days after cell inoculation | 4/4 | 13/14 | 26/26 |
| Number of mice with tumors of ≧ 5 mm³ 30 days after cell inoculation | 4/4 | 13/14 | 26/26 |

Data are means ± SE.

2-9. Effects of OGF on Tumor Latency, Incidence and Growth

Latency time until the development of visible tumors differed significantly between OGF-treated and control animals (Table 8), with OGF-treated mice developing tumors more than 3 days later than controls. The interval of time from tumor cell inoculation to initial tumor appearance was 43% longer for animals receiving OGF than mice given sterile water, such that mice treated with OGF had a latency of 15.2 days relative to a 10.6 day latency for control animals. Latency times until tumor appearance reached 62.5 mm³ were significantly increased for the OGF group from control levels, being nearly 41% longer for these mice relative to the control group (Table 8). Seven days after tumor cell inoculation, 30% of the control mice exhibited an initial tumor appearance, whereas no mouse receiving QGF had a tumor measuring ≧5 mm³; these differences were statistically significant at P<0.05 (Table 8). Fifteen days after tumor cell inoculation, all of the control mice displayed an initial tumor appearance, but less than 62% of the OGF treated mice had a tumor measuring ≧5 mm³. At the termination of the experiment on day 30, one mouse receiving OGF did not have a tumor, this difference between OGF treated and control animals was not significant.

TABLE 8

Latency and Incidence of Tumor Appearance in Nude Mice
Inoculated with BxPC-3 Human Pancreatic Tumor Cells and
Treated with 5 mg/kg OGF Three Times Daily or Sterile Water

| | Control | OGF |
|---|---|---|
| Latency (days) for visible tumor[a] | 9.4 ± 1.1 | 12.7 ± 1.4** |
| Latency (days) for initial tumor appearance[a] | 10.6 ± 1.1 | 15.2 ± 1.2** |
| Latency (days) for tumors of 62.5 mm³ in size[a] | 12.2 ± 0.8 | 17.2 ± 1.1** |
| Number of mice with tumors 7 days after tumor cell inoculation[b] | 3/10* | 0/13* |
| Number of mice with tumors 14 days after tumor cell inoculation[b] | 8/10 | 5/13* |
| Number of mice with tumors 15 days after tumor cell inoculation[b] | 10/10 | 8/13* |
| Number of mice with tumors 22 days after tumor cell inoculation[b] | 10/10 | 12/13 |
| Number of mice with tumors 30 days after tumor cell inoculation[b] | 10/10 | 12/13 |

[a]Data are means ± SE. Values were analyzed using one-way analysis of variance with subsequent comparisons made with Newman Keuls tests.
[b]All tumors were ± 5 mm³. Data were analyzed using chi-square tests.
*, **Significantly different from the control group at *P < 0.05 and **P < 0.01.

Although mean tumor volumes for mice receiving OGF were smaller at every time point measured, no significant differences were established between the OGF and control groups within the 30 days of the experiment (data not shown).

The body weights of mice given OGF were comparable to the those receiving sterile water. No behavioral abnormalities (e.g. hyperactivity, biting) were noted in either group. No metastases or lesions were found in either the OGF or control groups.

2-10. Quantitation of the ζ Opioid Receptor

Figure 17:
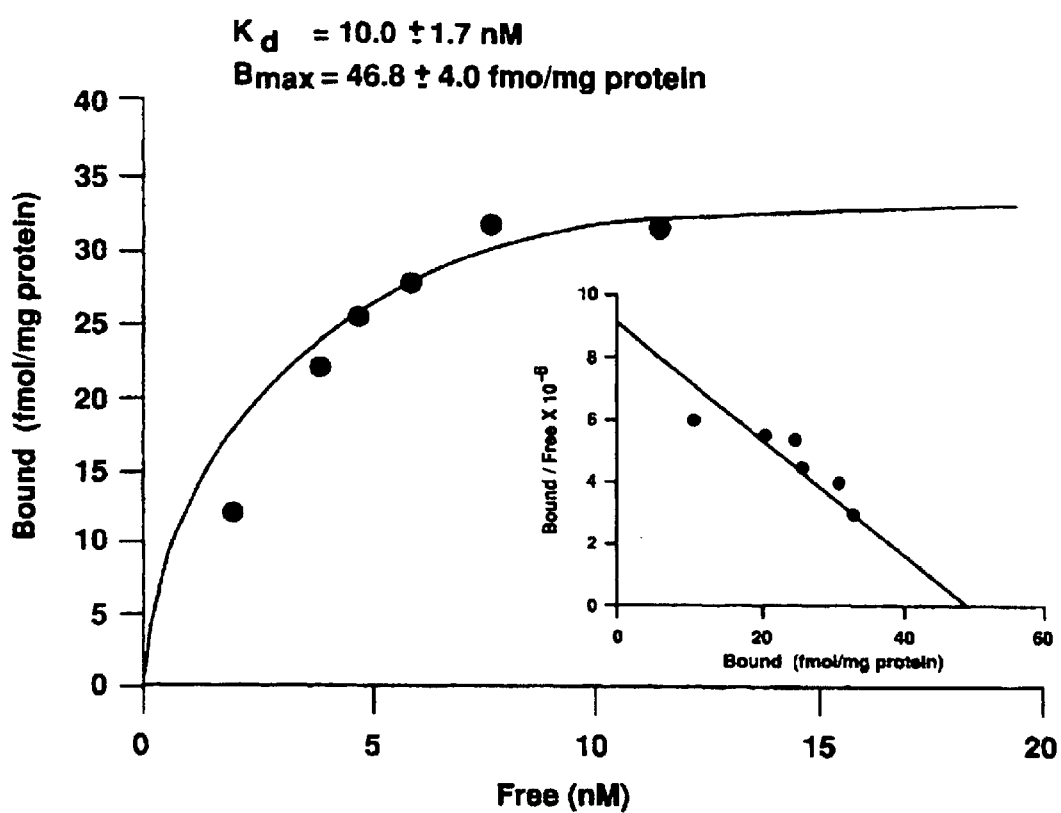
FIG. 17 graphically depicts representative saturation isotherm of specific binding of [$^3$H]-[Met$^5$]-enkephalin to nuclear homogenates of BxPC-3 human pancreatic tumors. Mean±SE binding affinity ($K_d$) and binding capacity ($B_{max}$) values from four experiments performed in duplicate are shown. Representative Scatchard plot of specific binding of radiolabeled [Met$^5$]-enkephalin to BxPC-3 nuclear homogenates revealed a one-site model of binding.

Tumor tissue removed from mice in each group days after tumor cell inoculation was assayed for the presence of ζ opioid receptors using [$^3$H-Met$^5$]enkephalin. Saturation isotherms for tumor tissue obtained from control animals indicated specific and saturable binding to the nuclear homogenates (FIG. 17). Analysis revealed a one-site binding model with a binding affinity ($K_d$) of 10.0±1.7 nM and a binding capacity ($B_{max}$) of 46.8±4.0 fmol/mg protein.

Figure 18:
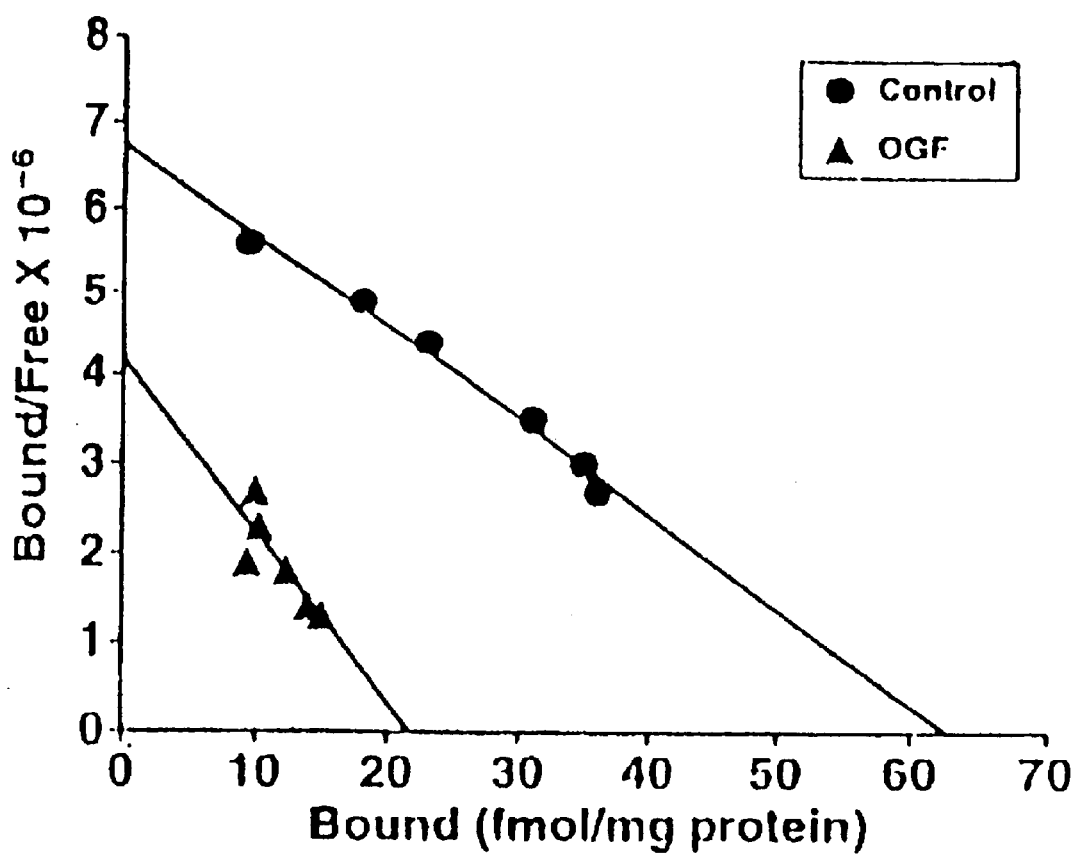
FIG. 18 graphically depicts representative Scatchard plots of the binding of [$^3$H]-[Met$^5$]-enkephalin to nuclear homogenates of BxPC-3 human pancreatic tumors removed from nude mice receiving either 5 mg/kg OGF three times daily (OGF) or sterile water (control).

Comparison of tumor homogenates from the OGF and control groups demonstrated a significant reduction in binding sites in tumors from OGF-treated mice (FIG. 18, Table 9). Binding affinity did not differ between the two groups, but were reduced 58% from control levels (Table 9).

TABLE 9

[$^3$H-Met$^5$]-Enkephalin Binding in Homogenates
of BxPC-3 Human Pancreatic Tumors from
Nude Mice Treated with 5 mg/kg OGF
Three Times Daily or Sterile Water

| | $B_{max}$ (fmol/mg protein) | $K_d$ (nM) |
|---|---|---|
| Control | 58.8 ± 6.9 | 11.4 ± 1.8 |
| OGF | 24.6 ± 5.2** | 7.1 ± 1.3 |

Values are means ± SE from at least three independent assays.
**Significantly different from the control group at P < 0.01.

12-11. Radioimmunoassay Levels of [Met$^5$]Enkephalin

Figure 19:
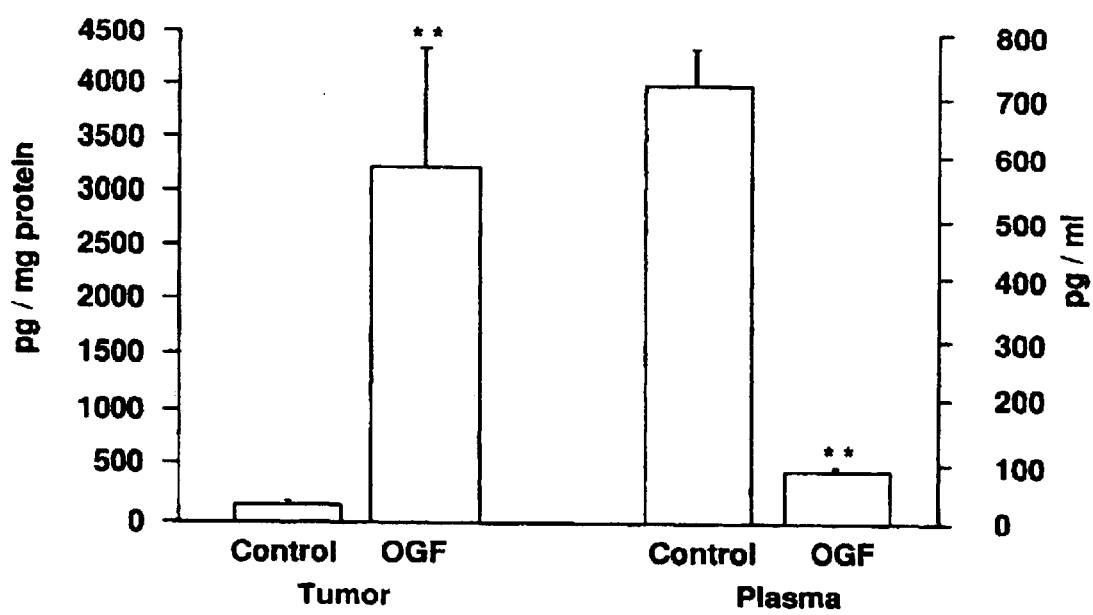
FIG. 19 graphically depicts radioimmunoassay levels of [Met$^5$]-enkephalin in tumors and plasma from nude mice transplanted with BxPC-3 human pancreatic cancer cells and injected with 5 mg/kg OGF three times daily (OGF) or sterile water (control). Values represent means±SE for at least four samples. **Significantly different from controls at p<0.01.
Figure 21:
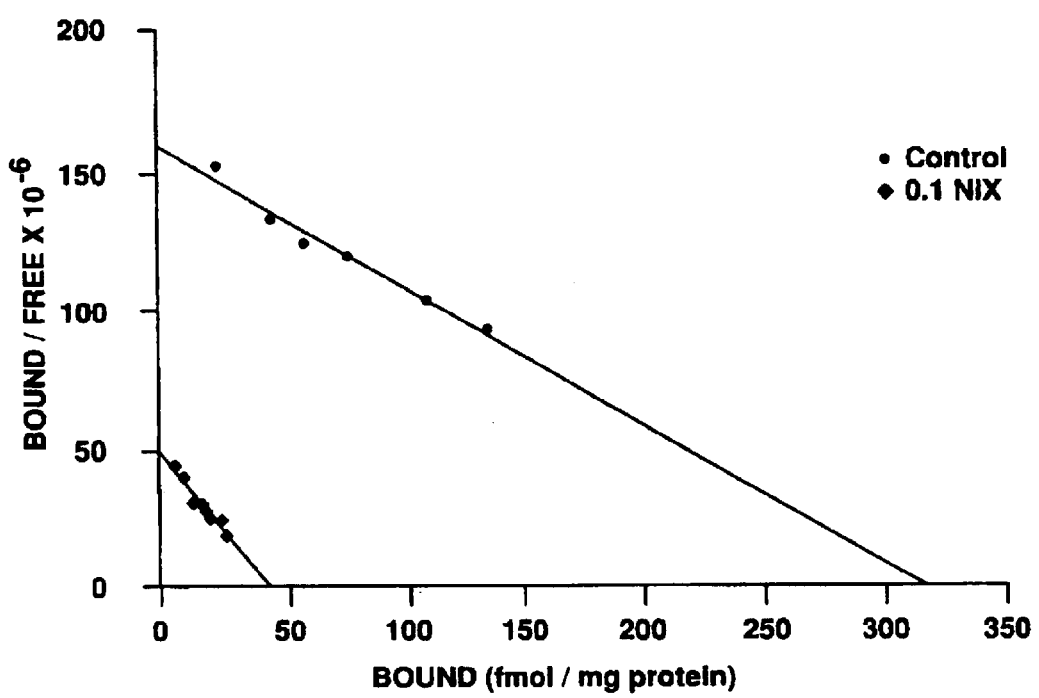
FIG. 21 graphically depicts representative Scatchard plots of the binding of [$^3$]-[Met$^5$]-enkephalin to HT-29 human colon tumors xenografted into nude mice receiving either 0.1 mg/kg NTX or sterile water beginning immediately after tumor cell inoculation. See Table 11 for $K_d$ and $B_{max}$ values.

Analysis of the peptide levels in both plasma and tumor tissue from OGF-treated and control mice indicated significant differences between groups (FIG. 19). Peptide levels were markedly elevated (P<0.001) in tumors from OGF-exposed mice being 24-fold greater than in control animals. Conversely, plasma levels of [Met$^5$]enkephalin were 8.6-fold greater in control mice than in animals receiving OGF (84.0±5.3 pg/ml). The plasma levels of [Met$^5$]enkephalin in normal (i.e. not injected with tumor cells) nude mice were 162.2±30.0 pg/ml, but this was 4.4-fold less than in tumor-bearing control animals.

2-12. Presence and Distribution of OGF and the ζ Opioid Receptor

Light microscopic observations of the hematoxylin and eosin stained sections of BxPC-3 tumors indicated that the tissue was a well-differentiated adenocarcinoma with gland-forming areas comprised of columnar epithelial cells without keratinization (FIG. 20A). Bands of fibrous connective tissue separated nests of tumor cells.

Utilizing immunocytochemistry, the presence and distribution of peptide (FIG. 20B) and receptor (FIG. 20D) were determined. Immunostaining was intense in the cytoplasmic region of the epithelial cells, with little or no reactivity in nuclei. Patterns of staining for OGF resembled those observed for the ζ opioid receptor. Specimens processed with antibodies to [Met]enkephalin or the ζ opioid receptor that were preabsorbed with their respective antigens (FIG. 20C, E), as well as tumor tissues stained only with secondary antibody (data not shown), had little immunofluorescence.

The present results are the first to show that an endogenous opioid system governs the growth of human pancreatic neoplasia. Our data reveal that an opioid peptide, [Met$^5$]-enkephalin, exerts a profound inhibition on the initiation and progression of human pancreatic tumors induced by inoculation of BxPC-3 cells into nude mice. Daily injections of OGF beginning at the time of tumor cell inoculation prevented the appearance of a tumor for a one-third longer time than controls, and at the termination of the experiments one animal given OGF did not have a tumor. Thus, even on day 15 when 100% of the controls had a tumor, almost 40% of the OGF-treated animals did not have a neoplasia. Although the tumors in the OGF-exposed animals were smaller than that of controls, no significant differences could be detected in the 30 day examination period.

EXAMPLE 3

Intermittent Blockade With Naltrexone Inhibits Colon Cancer 3-1. Animals and Tumors HT-29 human colon cancer cells, purchased from the American Type Culture Collection (Rockville, Md.), were grown in McCoy's 5A Modified Medium containing 10% fetal calf serum, L-glutamine (2 mM), penicillin (10 units/ml), and streptomycin (100 mg/ml) in an atmosphere of 7% $CO_2$ at 37° C. Cell viability was determined by the trypan blue exclusion test. Five- to six-week-old male athymic nude mice, obtained from the National Cancer Institute (Frederick, Md.), were injected subcutaneously over the right shoulder with 1×10$^6$ log phase HT-29 cells in a 0.5 ml suspension of McCoy's media. The day of tumor cell inoculation was considered day 0. The mice were evaluated daily and the date that the tumor became palpable was recorded. The time of "initial" appearance of a tumor was considered to be the day when tumor volume was 5 mm$^3$ or larger. Individual tumors were measured with vernier calipers every 2 days. Measurements of the two largest perpendicular dimensions were recorded and tumors volume was calculated using the formula: length×(width)$^2$×0.5 [Osieka, R., D. P. Houchens, and A. Goldin. Chemotherapy of human colon cancer xenografts in athymic nude mice. *Cancer* 40:2640–2650, (1977)]. All mice were euthanized and necropsied 50 days after tumor cell inoculation. Tumor tissue for receptor binding assays and radioimmunoassays was rapidly frozen in liquid nitrogen and stored at −70° C. until assayed. Blood was obtained from the inferior vena cava of each mouse, centrifuged in EDTA-coated tubes, and plasma was frozen for radioimmunoassay.

3-2. Drugs and Drug Treatment

Treatment was initiated on the day of tumor cell inoculation. Mice received a daily subcutaneous injection of 0.1 mg/kg naltrexone (0.1 naltrexone group), or an equal volume of vehicle (i.e., sterile water); injections were administered in the left flank. Animals were weighed-weekly and appropriate dosage adjustments made.

3-3. Receptor Binding Assays

Receptor binding assays were performed according to procedures reported elsewhere [Zagon, I. S. and P. J. McLaughlin. Endogenous opioid systems regulate growth of neural tumor cells in culture. *Brain Res.* 490:1313–1318 (1988)]. Briefly, nuclear homogenates were incubated for 150 minutes at 22° C. with tritiated [Met$^5$]-enkephalin in the presence or absence of 100 nM unlabeled [Met$^5$]-enkephalin. At least three independent assays were performed on tumors from mice treated with 0.1 mg/kg naltrexone or sterile water.

3-4. Radioimmunoassays of [Met$^5$]-Enkephalin

Radioimmunoassays were performed to examine the presence and concentration of [Met$^5$]-enkephalin in plasma and tumor tissue of animals given 0.1 mg/kg naltrexone or sterile water. Tissue and plasma [Met$^5$]-enkephalin levels were determined with reagent kits from IncStar Corporation (Stillwater, Minn.) according to procedures described previously [Zagon, I. S. and P. J. McLaughlin. Opioid antagonist modulation of murine neuroblastoma: a profile of cell proliferation and opioid peptides and receptors. *Brain Res.* 480:16–28 (1989)]. Specificity of the assay was 100% activity for [Met$^5$]-enkephalin, and a cross-reactivity of 2.8% with [Leu$^5$]-enkephalin, 0.1% with β-endorphin (β-lipotropin (61–77)), and less than 0.002% with γ-endorphin, α-neoendorphin, substance P, and porcine dynorphin 1–13.

3-5. Statistical Analysis

Latencies until tumor appearance were analyzed using one-way analysis of variance; subsequent comparisons were made with the Newman-Keuls test. The number of mice developing tumors was expressed as a ratio of the total number of mice in the group. Comparisons between groups were made with chi-square tests.

The growth of tumors was compared for each mouse beginning on the day of initial tumor appearance and every 3 days thereafter until the termination of the experiment. Tumor measurements on these days were analyzed using one-way analysis of variance and Newman-Keuls test. Body weights were compared with a two-factor analysis of variance.

Receptor binding data were analyzed with a Lundon (Saturation Isotherm Binding Analysis) computer program (Lundon Software, Cleveland, Ohio). This analysis utilizes non-linear least squares regression. Saturation curves and Scatchard plots were computed and plotted directly by this program.

Data from radioimmunoassays were evaluated by analysis of variance. Subsequent comparisons between groups were computed manually using the Newman-Keuls test.

EXAMPLE A

Tumor Incidence, Latency and Growth

Ten days after tumor cell inoculation all mice in the control group had palpable tumors; on this same day, only 2 of the mice in the 0.1 naltrexone group has tumors which were palpable. The mean latency prior to palpable tumor appearance for mice treated with 0.1 mg/kg naltrexone was increased 2.4-fold compared to control mice (Table 10). Mice in the 0.1 naltrexone group also exhibited increases of 76% relative to control animals with respect to the time when a tumor reached a size of at least 5 mm$^3$. Moreover, the range in latency until initial tumor appearance for mice: in the 0.1 naltrexone group was up to 2-fold greater than control animals. The interval between palpable tumors and initial tumor appearance, however, was similar for the 0.1 naltrexone and control groups of mice.

Nineteen days after tumor cell inoculation, 100% of the control mice had a tumor of 5 mm$^3$ or larger in contrast to the 0.1 naltrexone group in which 30% of the mice had tumors (Table 10). Five weeks after tumor cell inoculation (i.e., day 36) 60% of mice receiving 0.1 mg/kg naltrexone had tumors and, at the conclusion of the study (i.e., day 50), 20% of the mice in the 0.1 haltrexone group still did not have tumors.

The size of tumors after initial tumor appearance did not differ between mice in the 0.1 naltrexone and control groups. Additionally, the body weights of mice given 0.1 mg/kg naltrexone were comparable to those of control animals throughout the experiment. Finally, there appeared to be no behavioral differences (e.g. hyperactivity) between mice in the 0.1 naltrexone and control groups.

TABLE 10

Tumor incidence and latency in nude mice with HT-29 colon tumors treated with 0.1 mg/kg NTX beginning immediately after tumor cell inoculation

|  | Control Group | 0.1 NTX Group |
| --- | --- | --- |
| Latency (days) for palpable tumor[a] | 7.1 ± 0.6 | 17.0 ± 2.8** |
| Latency (days) for initial tumor appearance[a] | 13.1 ± 0.9 | 23.1 ± 2.9** |
| (Range) | (10–19) | (14–37) |
| Number of mice with tumors 19 days after inoculation[b] | 10/10 | 3/10** |
| Number of mice with tumors 36 days after inoculation[b] | 10/10 | 6/10* |
| Number of mice with tumors 50 days after inoculation[b] | 10/10 | 8/10 |

[a]Data are means ± S.E. from 10 mice. Data were analyzed using one-way analysis of variance with subsequent comparisons made with Newman-Keuls tests.
[b]Data were analyzed using chi-square tests.
Significantly different from the control group at $p < 0.01$ (**) and $p < 0.05$ (*).

EXAMPLE B

Receptor Binding Assays

Receptors in tumor tissue from animals exposed to 0.1 mg/kg naltrexone did not differ from control levels in their binding affinity (i.e., $K_d$) for [$^3$H]-[Met$^5$]-enkephalin (Table 11). However, the binding capacity (i.e., $B_{max}$) of the receptors in tumor tissue harvested from animals given 0.1 mg/kg naltrexone was decreased 6.6-fold from control values (Table 21).

TABLE 11

[$^3$H]-[Met$^5$]-enkephalin binding of HT-29 tumor homogenates from nude mice treated with 0.1 mg/kg NTX beginning immediately after tumor cell inoculation

|  | $B_{max}$ (fmol/mg protein) | $K_d$ (nM) |
| --- | --- | --- |
| Control | 326.3 ± 21.1 | 20.5 ± 2.0 |
| 0.1 NTX | 52.9 ± 12.1** | 12.2 ± 2.2 |

Values represent means ± S.E. from at least 3 independent assays. Significantly (different from the control group at $p < 0.01$ (**).

EXAMPLE C

Radioimmunoassays for [Met$^5$]-Enkephalin

Plasma [Met$^5$]-enkephalin levels in mice treated with 0.1 mg/kg naltrexone were elevated. 2.5-fold from control values (Table 12). Although [Met$^5$]-enkephalin levels in tumor tissue from mice given 0.1 mg/kg naltrexone were increased 34% from controls, no statistical difference was noted (Table 12).

TABLE 12

[Met$^5$]-enkephalin levels in tumors and plasma from nude mice transplanted with HT-29 colon cancer cells and exposed to 0.1 mg/kg NTX beginning immediately after tumor cell inoculation

|  | Tissue [Met$^5$]-enkephalin (pg/mg tissue) | Plasma [Met$^5$]-enkephalin (pg/ml plasma) |
| --- | --- | --- |
| Control | 59.3 ± 6.2 | 40.3 ± 10.7 |
| 0.1 NTX | 79.2 ± 5.2 | 100.0 ± 20.0* |

Values represent means ± S.E. for radioimmunoassay levels for at least 4 samples. Significantly different from controls at $p < 0.05$ (*).

EXAMPLE 4

[Met$^5$]-Enkephalin Inhibits Colon Cancer 4-1. Tumor Cells and Xenografts

HT-29 human colon cancer cells were obtained from the American Type Culture Collection (Rockville, Md.). HT-29 cells were grown in McCoys 5A media (modified), containing 10% fetal calf serum, 2 mM L-glutamine, 1.2% sodium bicarbonate and antibiotics (11 U/ml penicillin, 10 μg/ml streptomycin, 10 μg/ml neomycin) in a humidified atmosphere of 7% $CO_2$-93% air at 37° C. Log-phase HT-29 cells were injected subcutaneously over the right shoulder ($10^6$ cells in a 0.5-ml suspension of McCoys media) into athymic NCr-nu male mice of 5–6 wk of age (National Cancer Institute, Frederick, Md.). All animals were allowed 1 wk to acclimate before experimentation, and food and water were available ad libitum.

Mice were evaluated daily, and the dates that the tumor became; palpable, visible, and measurable were recorded. The time of measurable tumor appearance was considered to be the day the tumor measured at least 5 mm$^3$. Animals were weighed weekly, and the tumors were measured three times per week. Measurements of the two largest perpendicular dimensions were recorded with vernier calipers (accuracy ±0.05 mm), and tumor volume was calculated using the formula length×(width)$^{2\times0.5}$. Mice were killed with $CO_2$ 50 days after tumor cell inoculation, and tissues were harvested for immunocytochemistry.

4-2. Drugs and Drug Treatment

Beginning on the day of tumor cell inoculation, animals were randomly divided into groups and received daily injections into the left shoulder of 0.5, 5, or 25 mg/kg [Met$^5$]-enkephalin, 5 mg/kg [Met$^5$]-enkephalin and 10 mg/kg naloxone, or 10 mg/kg naloxone; controls received an equivalent volume of sterile water. All drugs were prepared weekly by dissolving the powders in sterile water.

4-3. Immunocytochemistry

To examine the presence of the OGF, [Met$^5$]-enkephalin, and the ζ-opioid receptor, immunocytochemistry was performed. Samples of tumor tissue were frozen in isopentane chilled on dry ice and stored at −70° C. for no longer than 1 wk. Specimens were sectioned (10 μm), fixed and permeabilized in 95% ethanol and acetone at −20° C., and blocked with Sorenson's phosphate buffer (SPB) and 3% normal goat serum in 0.1% Triton X-100 at room temperature for 15 min. Ammonium sulfate-purified anti-[Met$^5$]-enkephalin immunoglobulin G (IgG)or anti-ζ-receptor IgG were diluted (1:100) in SPB with 1% normal goat serum in 0.1% Triton X-100. Details about the production and characteristics of the polyclonal antibodies to [Met$^5$]-enkephalin (CO-172) and ζ-receptor (AO-440) have been reported elsewhere (26, 30, 31). Control sections were stained with antibodies preabsorbed with an excess of antigen (i.e., [Met$^5$]-enkephalin or the 4 subunits of the ζ-receptor) or processed only with the secondary antibody.

4-4. Human Tissue

Human colon cancer tissues were obtained from surgical resections. Research protocols were approved by the Clinical Investigation Committee of The M.S. Hershey Medical Center of The Pennsylvania State University. Patients included an 82-yr-old male with a poorly differentiated cecal adenocarcinoma, an 84-yr-old female with a poorly differentiated sigmoid adenocarcinoma, and a 55-yr-old male with a moderately differentiated sigmoid adenocarcinoma. The tumor tissue was stored at −70° C. for no more than 7 days before immunocytochemistry was conducted. The histology of the adenocarcinomas was assessed by observation of hematoxylin-eosin-stained sections.

4-5. Analysis and Statistics

The number of mice developing tumors (incidence) was expressed as a ratio of the total number of mice in the group. Comparisons between groups were made with chi-square tests. Latencies until a palpable tumor was detected, a visible tumor was present, or a measurable tumor appeared were compared between groups of mice using a one-way analysis of variance. Tumor volumes were analyzed using a one-way analysis of variance. Subsequent comparisons between groups were computed with Newman-Keuls tests.

4-6. Tumor Burden Studies

Figure 22:
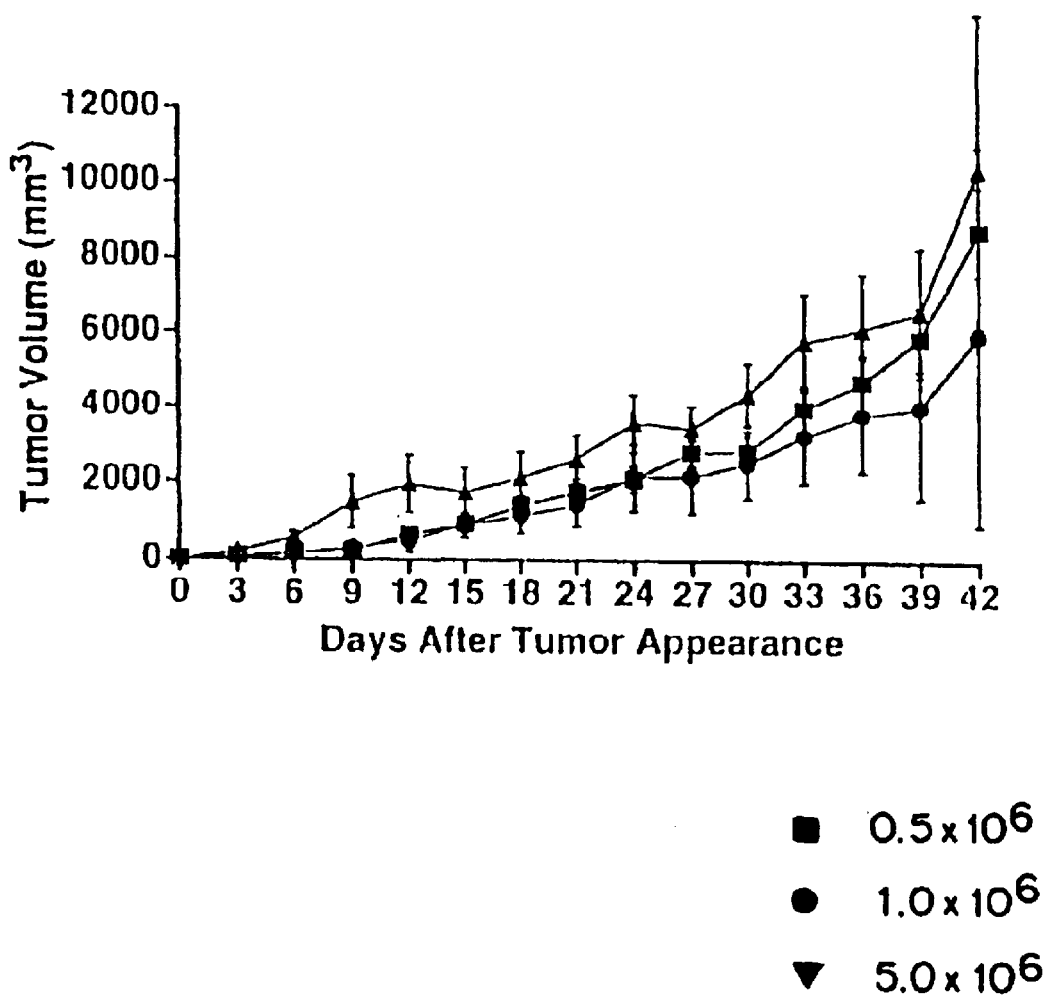
FIG. 22 graphically depicts growth of measurable human colon cancer xenografts in nude mice after inoculation of 0.5, 1, and 5×10$^{-6}$ HT-29 cells. Measurements were taken on the day of initial tumor appearance and every 3 days thereafter. Data represent means±SE for 5–7 animals in each group.

Before experimentation with OGF, the relationship between the number of tumor cells inoculated into nude mice and the characteristics of tumorigenicity were explored in animals receiving 0.5, 1, or 5×10$^6$ HT-29 colon cancer cells. Dose-response effects for latencies of palpable, visible, and measurable tumor formation, incidence of neoplasia, and the size of tumor (i.e. volume) were detected (Table 13, FIG. 22). Although tumors often appeared to occur earlier in mice injected with 5×10$^6$ than 1×10$^6$ HT-29 cells, no significant differences were noted. However, when tumor burden was reduced to 0.5×10$^5$ cells, mean latencies for palpable and visible tumor formation, the latency for initial tumor appearance, and the number of mice with neoplasia 15 days after inoculation with HT-29 cells were significantly different from mice receiving 1 or 5×10$^6$ cells. Based on these results, all subsequent experiments studying the effects of OGF were performed with animals injected with 1×10$^6$ HT-29 colon cancer cells.

TABLE 13

Tumor latency and incidence in nude mice inoculated with different numbers of HT-29 human colon cells

|  | 0.5 × 10$^6$ Cells | 1 × 10$^6$ Cells | 5 × 10$^6$ Cells |
| --- | --- | --- | --- |
| Latency for palpable tumor, days | 11.4 ± 1.7* | 7.0 ± 0.4 | 5.4 ± 0.2 |
| Latency for visible tumor, days | 12.8 ± 1.1* | 8.4 ± 0.4 | 6.9 ± 0.1 |

TABLE 13-continued

Tumor latency and incidence in nude mice inoculated with different numbers of HT-29 human colon cells

|  | 0.5 × 10$^6$ Cells | 1 × 10$^6$ Cells | 5 × 10$^6$ Cells |
| --- | --- | --- | --- |
| Latency for measurable tumor appearance, days | 14.2 ± 1.8* (11–20) | 9.7 ± 0.3 (9–11) | 7.6 ± 0.1 (8–9) |
| No. of mice with tumors 15 days after inoculation | 2/7* | 7/7 | 7/7 |
| No. of mice with tumors 50 days after inoculation | 5/7 | 7/7 | 7/7 |

Data for latency represent means ± SE (n = 7/group). Range shown in parentheses. *Significantly different from other two groups at $P < 0.01$.

4-7. OGF and Tumorigenicity

Figure 23:
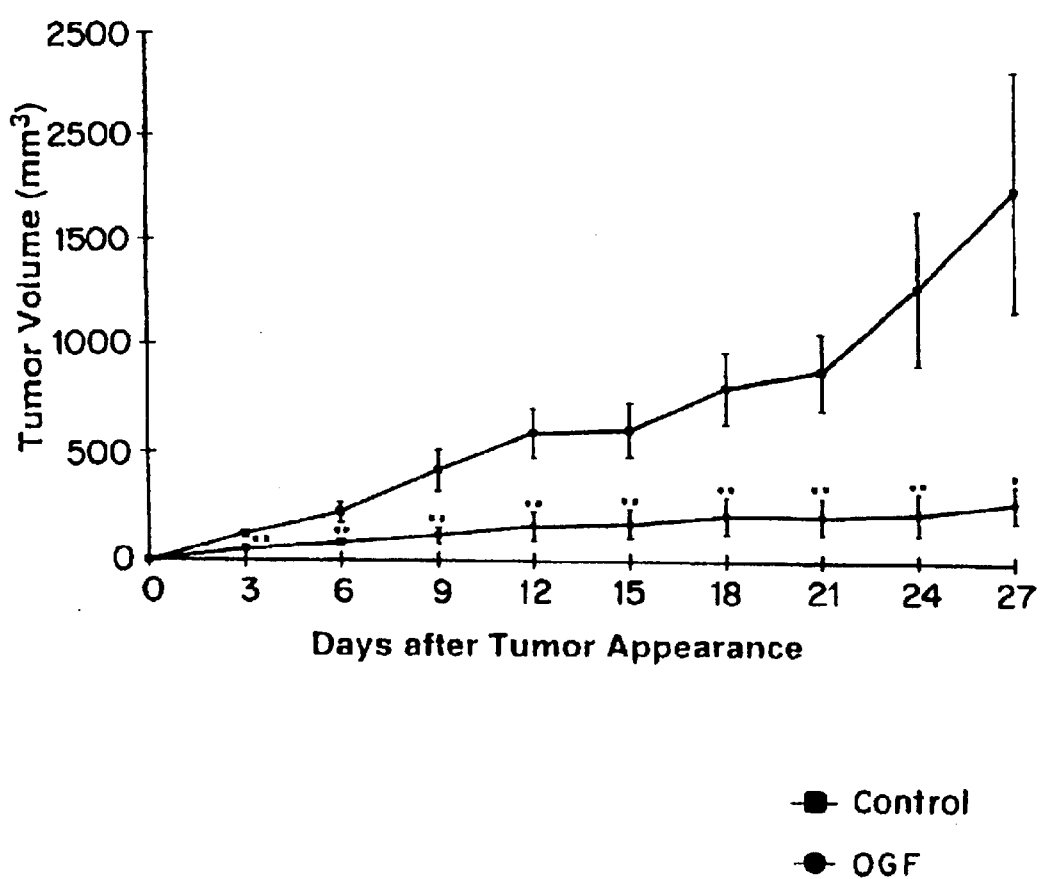
FIG. 23 graphically depicts growth of measurable human colon cancer xenografts in nude mice after inoculation of 1×10$^6$ HT-29 cells and daily treatment with opioid growth factor (OGF) or an equivalent volume of water (control). Data for OGF reflect tumor volumes from mice receiving 0.5, 5, or 25 mg/kg OGF because no differences were detected between OGF groups. Measurements were taken on the day of initial tumor appearance and every 3 days thereafter. Data represents means±SE for 13 animals in the control group and 18 mice in the OGF group. *Significantly different from controls at P<0.05; **significantly different from controls at P<0.01.

To examine the influence of OGF, [Met$^5$]-enkephalin, on colon cancer, nude mice receiving xenografts of HT-29 cells were given daily injections of 0.5, 5 or 25 mg/kg OGF or an equivalent volume of sterile water (controls) beginning on the day of tumor cell inoculation (Table 14, FIG. 23). Animals given OGF exhibited marked reductions in tumor incidence and delays in oncogenesis, but no distinct dose-response effect was observed within the 50-fold dose range of peptide utilized in contrast to mice in the control group in which 93% of the subjects displayed a measurable tumor by day 21, only 14–28% of the mice given OGF had a tumor. In fact, even at the termination of the experiment 50 days after tumor cell inoculation, only 36–50% of the animals receiving 0.5, 5, or 25 mg/kg OGF had a tumor. Thus more than one-half (57%) of all the mice given daily injections of OGF never-developed xenografts of colon cancer, compared with 93% of the controls within the 7-wk experimental period. In mice given OGF and displaying tumors, delays from controls ranged from 82 to 116%, 80 to 105%, and 79 to 126% in latencies for palpable, visible, and measurable tumors, respectively.

Examination of tumor volume data showed that the OGF-treated animals had a significant and consistent reduction in tumor size compared with the control group. Because no differences were found between groups treated with 0.5, 5, or 25 mg/kg OGF, these results were collapsed and compared with control levels (FIG. 23). Beginning 3 days after detection of a measurable cancer, mice given OGF differed significantly from controls, with decreases in tumor volume ranging from 57 to 84% recorded from 3 to 27 days after appearance of a measurable tumor.

To determine whether OGF was influencing the incidence and progression of HT-29 colon cancer xenografts, some animals received daily injections of the short-acting opioid antagonist naloxone (10 mg/kg) concomitantly with OGF (5 mg/kg) or 10 mg/kg naloxone alone (Table 14). No differences in latencies of palpable, visible, or measurable tumors or the incidence of cancer were noted between these two groups of subjects and control mice given sterile water (Table 14). The size of tumors also did not differ between animals given OGF and naloxone or naloxone alone and the control subjects at any time point monitored. Thus 50 days after inoculation of HT-29 cells, mice given 5 mg/kg OGF and 10 mg/kg naloxone or 10 mg/kg naloxone alone had tumor volumes (1,589±858 and 1,494±517 mm$^3$, respectively) comparable to controls (1,767±586 mm$^3$).

TABLE 14

Tumor latency and incidence in nude mice inoculated with $1 \times 10^6$ HT-29 human colon cancer cells and treated with either various doses of OGF [Met$^5$]enkephalin) and/or naloxone or an equivalent volume of sterile water (control)

|  | Control | 0.5 mg/kg OCF | 5 mg/kg OCF | 25 mg/kg OCF | 5 mg/kg OCF + 10 mg/kg Nal | 10 mg/kg Nal |
|---|---|---|---|---|---|---|
| Latency for palpable tumor, days | 10.2 ± 1.6 | 18.6 ± 3.2* | 19.2 ± 2.2 | 22.0 ± 4.5* | 13.7 ± 1.6 | 9.3 ± 1.4 |
| Latency for visible tumor, days | 11.2 ± 1.6 | 22.4 ± 2.6† | 20.2 ± 2.2* | 23.0 ± 4.5† | 14.5 ± 0.9 | 10.3 ± 1.4 |
| Latency for measurable tumor appearance, days | 12.4 ± 1.4 (6–19) | 28.0 ± 0.0† (28) | 22.2 ± 2.3† (13–22) | 24.0 ± 4.5† (12–32) | 15.6 ± 0.9 (13–20) | 12.8 ± 1.3 (10–16) |
| No. of mice with tumors 21 days after inoculation | 13/14 | 2/14† | 4/14† | 2/14† | 7/8 | 4/5 |
| No. of mice with tumors 50 days after inoculation | 13/14 | 7/14* | 6/14† | 6/14† | 7/8 | 4/5 |

Data for latencies represent means ± SE. Range shown in parentheses. OCF, opoid growth factor, Nal, naloxone, n = 14 for OGF alone, 8 for OCT + Nal, 5 for Nal alone, and 14 for control. *Significantly different from controls at $P < 0.05$; *significantly different from controls at $P < 0.01$.

Figure 24A:
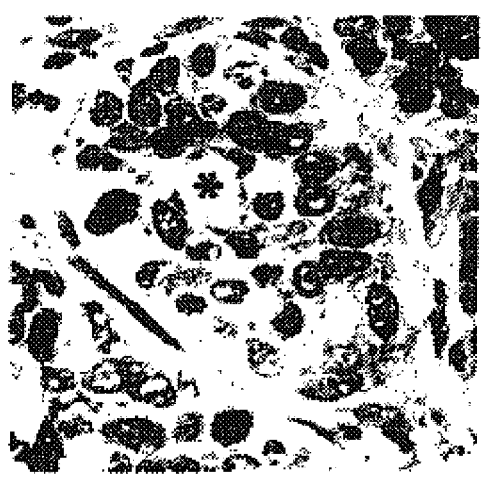
FIG. 24 are photomicrographs of HT-29 colon neoplasia xenografts. A: hematoxylin-stained section showing cancer cells arranged in a glandular pattern. *lumen of gland. B: section stained with a polyclonal antibody of [Met$^5$]-enkephalin (1:200) and a secondary antibody of peroxidase-conjugated goat anti-rabbit immunoglobulin (IgG)(1:50). Note staining of the cytoplasm in cells (arrows) and lack of immunoreactivity associated with the nucleus. C: control section stained with antibody to [Met$^5$]-enkephalin that was preabsorbed with [Met$^5$]-enkephalin. Magnification and times of exposure and printing were similar to those in B. D: specimen processed with a polyclonal antibody to the 17-kDa subunit of the ζ-opioid receptor (1:200) and a secondary antibody of peroxidase-conjugated goat anti-rabbit IgG (1:100). The cytoplasm of the cells was immunoreactive (arrows), but not the cell nuclei. E: control preparation stained with an antibody to the ζ-receptor preabsorbed with protein of the 32, 30, 17, and 16 kDa subunits; no immunoreactivity can be observed. Bar=24 µm.
Figures 24B, 24C:
Figures 24D, 24E:
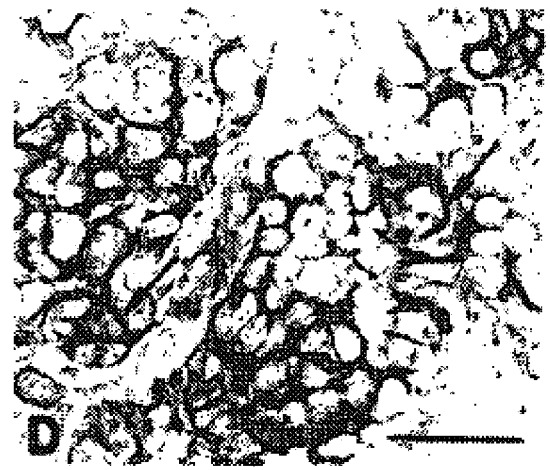

4-8. Presence and Location of the OGF and the ζ-Opioid Receptor in Xenografts of HT-28 Tumors The distribution of OGF ([Met$^5$]-enkephalin) and ζ-opioid receptor was evaluated by immunocytochemical examination of tissue obtained from xenografts of HT-29 tumors (FIG. 24). Histologically, tumors induced by inoculation of HT-29 colon cancer cells exhibited cords of neoplastic epithelial cells arranged in tubular units separated by fibrous connective tissue stroma. Many cells contained large pleomorphic nuclei. Goblet cell differentiation was observed, and numerous cells contained periodic acid Schiff stain-positive material (data not shown). Sections of HT-29 tumors stained with antisera to [Met$^5$]-enkephalin revealed immunoreactivity associated with the cytoplasm of the adenocarcinoma cells, but not the nucleus. Tissue sections processed with antisera preabsorbed with [Met$^5$]-enkephalin or subjected to the secondary antibody had no staining. Immunostaining with antibodies to the ζ-opioid receptor exhibited a profile similar to that with antiserum to [Met$^5$]-enkephalin; antigen was associated with the cytoplasm, but not the nucleus. Sections of tumor processed with anti-ζ-receptor IgG preabsorbed with the subunits (32, 30, 17 and 16 kDa) of the ζ-receptor or only the secondary antibody exhibited no immunoreactivity.

4-9. Presence and Location of the the OGF in Surgical Specimens

Figure 25A:
FIG. 25 are photomicrographs of a surgical specimen of colon adenocarcinoma from an 82-year-old male patient. A: hematoxylin-stained section showing glandular arrangement of tumor cells. B: [Met$^5$]-enkephalin-like immunoreactivity can be observed in the cytoplasm (arrows), particularly in the apical cytoplasm, but not the nuclei of the colon cancer cells. C: sections stained with antisera to [Met$^5$]-enkephalin that was preabsorbed with an excess of [Met$^5$]-enkephalin; no immunoreactivity can be observed. Magnification and time of exposure and printing were similar to that in B. *lumen of gland. Bar=28 µm.
Figure 25B:
Figure 25C:
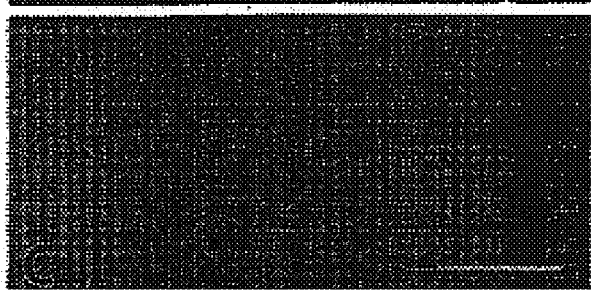

To assess the distribution of the OGF (i.e., [Met$^5$]-enkephalin) in colon cancer obtained directly from patients, specimens collected from surgical resections of colon adenocarcinoma were examined (FIG. 25). Immunocytochemical preparations revealed staining for [Met$^5$]-enkephalin in the cytoplasm, but not the nucleus, of colon cancer cells. Sections of tissue stained with antibodies to [Met$^5$]-enkephalin that were preabsorbed with antigen or only the secondary antibody had no immunoreactivity. Staining with anti-[Met$^5$]-enkephalin IgG was observed in tumor tissue samples representative of both poorly and moderately differentiated cancers. Although the number of specimens was extremely limited, with tissues from only three patients examined, neither the sex no age of the patient altered the presence or location of staining, with anti-[Met$^5$]-enkephalin IgG.

We claim:

1. A method for the treatment of a gastrointestinal cancer, wherein said cancer is characterized by the presence of at least one zeta receptor comprising administering [Met$^5$]-enkephalin in an amount sufficient to occupy said zeta receptor thereby inhibiting or arresting said cancer, and wherein said gastrointestinal cancer is colorectal cancer.

2. The method of claim 1 wherein said [Met$^5$]-enkephalin is administered in an amount between about 0.1 and 10 mg per day.

3. The method of claim 1 wherein the route of said administration is parenteral or intravenous.

4. The method of claim 3 wherein said administration is time-released.

5. The method of claim 4 wherein said [Met$^5$]-enkephalin is time-released by a patch, a microcapsule, an implant, a suspension or an osmotic pump.

* * * * *

UNITED STATES PATENT AND TRADEMARK OFFICE
CERTIFICATE OF CORRECTION

PATENT NO. : 6,737,397 B1  Page 1 of 1
APPLICATION NO. : 09/640622
DATED : May 18, 2004
INVENTOR(S) : Ian S. Zagon et al.

It is certified that error appears in the above-identified patent and that said Letters Patent is hereby corrected as shown below:

On the Title Page, Item (63): "08/827,841" should read --08,827,481--

Signed and Sealed this

Tenth Day of July, 2007

JON W. DUDAS
*Director of the United States Patent and Trademark Office*